(12) United States Patent
Bishop et al.

(10) Patent No.: US 11,938,039 B2
(45) Date of Patent: *Mar. 26, 2024

(54) IMPLANT WITH STRUCTURAL MEMBERS ARRANGED AROUND A RING

(71) Applicant: Institute for Musculoskeletal Science and Education, Ltd., King of Prussia, PA (US)

(72) Inventors: Sean S. Bishop, Malvern, PA (US); Christopher J. Ryan, Lincoln University, PA (US); Edward J. McShane, III, Collegeville, PA (US); Megan A. Stauffer, Wayne, PA (US); Joseph M. Nyahay, Eagleville, PA (US)

(73) Assignee: Institute for Musculoskeletal Science and Education, Ltd., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/566,146

(22) Filed: Dec. 30, 2021

(65) Prior Publication Data

US 2022/0117751 A1 Apr. 21, 2022

Related U.S. Application Data

(63) Continuation of application No. 16/725,790, filed on Dec. 23, 2019, now Pat. No. 11,213,405, which is a
(Continued)

(51) Int. Cl.
*A61F 2/44* (2006.01)
*A61F 2/30* (2006.01)
*A61F 2/46* (2006.01)

(52) U.S. Cl.
CPC ............ *A61F 2/447* (2013.01); *A61F 2/4455* (2013.01); *A61F 2002/302* (2013.01);
(Continued)

(58) Field of Classification Search
CPC .......... A61F 2/44; A61F 2/442; A61F 2/4455; A61F 2/446; A61F 2/4465; A61F 2/447
See application file for complete search history.

(56) References Cited

U.S. PATENT DOCUMENTS 3,720,959 A 3/1973 Hahn
4,038,703 A 8/1977 Bokros
(Continued)

FOREIGN PATENT DOCUMENTS

CN 101708138 5/2010
CN 103932841 7/2014
(Continued)

OTHER PUBLICATIONS

Office Action dated May 5, 2017 in U.S. Appl. No. 15/141,655.
(Continued)

*Primary Examiner* — Eric S Gibson
(74) *Attorney, Agent, or Firm* — Plumsea Law Group, LLC

(57) ABSTRACT

An implant may include a body including a ring, the ring further defining an opening, and the body defining a transverse plane dividing the implant into a superior half and an inferior half. The ring may also define a radial direction and a circumferential direction. The implant may further include a first outer member attached to the ring, wherein the first outer member extends radially from the ring, wherein the first outer member defines one or more arches, and wherein the ring further defines a central channel extending through the implant.

20 Claims, 19 Drawing Sheets

Related U.S. Application Data continuation of application No. 15/457,470, filed on Mar. 13, 2017, now Pat. No. 10,512,549.

(52) U.S. Cl.
CPC ............ *A61F 2002/30235* (2013.01); *A61F 2002/30289* (2013.01); *A61F 2002/30593* (2013.01); *A61F 2002/30784* (2013.01); *A61F 2002/3093* (2013.01); *A61F 2002/4495* (2013.01); *A61F 2002/4629* (2013.01)

(56) References Cited

U.S. PATENT DOCUMENTS

| | | | |
|---|---|---|---|
| 4,309,777 A | 1/1982 | Patil | |
| 4,759,769 A | 7/1988 | Hedman | |
| 4,851,008 A | 7/1989 | Johnson | |
| 4,889,685 A | 12/1989 | Shimamune | |
| 4,917,704 A | 4/1990 | Frey | |
| 4,961,740 A | 10/1990 | Ray et al. | |
| 5,055,104 A | 10/1991 | Ray | |
| 5,059,193 A | 10/1991 | Kuslich | |
| 5,198,308 A | 3/1993 | Shetty et al. | |
| 5,263,953 A | 11/1993 | Bagby | |
| 5,306,310 A | 4/1994 | Siebels | |
| 5,397,359 A | 3/1995 | Mittelmeier | |
| 5,423,817 A | 6/1995 | Lin | |
| 5,458,638 A | 10/1995 | Kuslich et al. | |
| 5,571,185 A | 11/1996 | Schug | |
| 5,571,192 A | 11/1996 | Schonhoffer | |
| 5,607,424 A | 3/1997 | Tropiano | |
| 5,609,635 A | 3/1997 | Michelson | |
| 5,609,636 A | 3/1997 | Kohrs | |
| 5,658,337 A | 8/1997 | Kohrs et al. | |
| 5,709,683 A | 1/1998 | Bagby | |
| 5,716,416 A | 2/1998 | Lin | |
| D403,069 S | 12/1998 | Drewry et al. | |
| 5,885,299 A | 3/1999 | Winslow | |
| 5,888,223 A | 3/1999 | Bray, Jr. | |
| 5,897,556 A | 4/1999 | Drewry et al. | |
| 5,954,504 A | 9/1999 | Misch et al. | |
| 5,968,098 A | 10/1999 | Winslow | |
| 5,973,222 A | 10/1999 | Devanathan et al. | |
| 6,010,502 A | 1/2000 | Bagby | |
| 6,039,762 A | 3/2000 | McKay | |
| 6,090,143 A | 7/2000 | Meriwether et al. | |
| 6,102,948 A | 8/2000 | Brosnahan, III | |
| 6,126,689 A | 10/2000 | Brett | |
| 6,149,651 A | 11/2000 | Drewry et al. | |
| 6,156,037 A | 12/2000 | LeHuec et al. | |
| 6,200,348 B1 | 3/2001 | Biedermann et al. | |
| 6,206,924 B1 | 3/2001 | Timm | |
| 6,210,412 B1 | 4/2001 | Michelson | |
| 6,371,987 B1 | 4/2002 | Weiland et al. | |
| 6,428,575 B2 | 8/2002 | Koo et al. | |
| 6,436,141 B2 | 8/2002 | Castro et al. | |
| 6,464,727 B1 * | 10/2002 | Sharkey ............... | A61F 2/446 623/17.11 |
| 6,468,309 B1 * | 10/2002 | Lieberman ............ | A61F 2/446 606/77 |
| 6,494,883 B1 | 12/2002 | Ferree | |
| 6,500,205 B1 | 12/2002 | Michelson | |
| 6,520,996 B1 | 2/2003 | Manasas et al. | |
| 6,527,805 B2 | 3/2003 | Studer et al. | |
| 6,530,956 B1 | 3/2003 | Mansmann | |
| 6,537,320 B1 | 3/2003 | Michelson | |
| 6,558,423 B1 | 5/2003 | Michelson | |
| 6,569,201 B2 | 5/2003 | Moumene | |
| 6,582,431 B1 | 6/2003 | Ray | |
| 6,582,467 B1 | 6/2003 | Teitelbaum et al. | |
| 6,585,770 B1 | 7/2003 | White et al. | |
| 6,616,695 B1 | 9/2003 | Crozet et al. | |
| 6,666,888 B1 | 12/2003 | Jackson | |
| 6,709,458 B2 | 3/2004 | Michelson | |
| 6,758,849 B1 | 7/2004 | Michelson | |
| 6,808,537 B2 | 10/2004 | Michelson | |
| 6,846,327 B2 | 1/2005 | Khandkar et al. | |
| 6,849,093 B2 | 2/2005 | Michelson | |
| 6,863,689 B2 | 3/2005 | Ralph et al. | |
| 6,923,810 B1 | 8/2005 | Michelson | |
| 6,962,606 B2 | 11/2005 | Michelson | |
| 6,997,953 B2 | 2/2006 | Chung et al. | |
| 7,135,043 B2 | 11/2006 | Nakahara et al. | |
| 7,141,068 B2 | 11/2006 | Ross et al. | |
| 7,153,325 B2 | 12/2006 | Kim et al. | |
| 7,186,267 B2 | 3/2007 | Aston et al. | |
| 7,241,313 B2 | 7/2007 | Unwin et al. | |
| 7,261,739 B2 | 8/2007 | Ralph | |
| 7,297,162 B2 | 11/2007 | Mujwid | |
| 7,341,601 B2 | 3/2008 | Eisermann et al. | |
| 7,410,501 B2 | 8/2008 | Michelson | |
| 7,429,270 B2 | 9/2008 | Baumgartner et al. | |
| 7,435,261 B1 | 10/2008 | Castro | |
| 7,452,369 B2 | 11/2008 | Barry | |
| 7,465,318 B2 | 12/2008 | Sennett et al. | |
| 7,485,134 B2 | 2/2009 | Simonson | |
| 7,527,649 B1 | 5/2009 | Blain | |
| 7,534,254 B1 | 5/2009 | Michelson | |
| 7,537,603 B2 | 5/2009 | Huebner et al. | |
| 7,537,616 B1 | 5/2009 | Branch et al. | |
| 7,575,598 B2 | 8/2009 | Albert | |
| 7,611,217 B2 | 11/2009 | Shamoun et al. | |
| 7,621,952 B2 | 11/2009 | Truckai et al. | |
| 7,621,953 B2 | 11/2009 | Braddock, Jr. et al. | |
| 7,628,814 B2 | 12/2009 | Studer et al. | |
| 7,645,475 B2 | 1/2010 | Prewett | |
| 7,655,043 B2 | 2/2010 | Peterman et al. | |
| 7,794,500 B2 | 9/2010 | Felix | |
| 7,799,056 B2 | 9/2010 | Sankaran | |
| 7,803,191 B2 | 9/2010 | Biedermann et al. | |
| 7,815,665 B2 | 10/2010 | Jahng | |
| 7,846,207 B2 | 12/2010 | Lechmann et al. | |
| 7,875,075 B2 | 1/2011 | Schwab | |
| 7,879,100 B2 | 2/2011 | Denoziere | |
| 7,879,103 B2 | 2/2011 | Gertzman et al. | |
| 7,935,149 B2 | 5/2011 | Michelson | |
| 8,016,887 B1 | 9/2011 | Castro | |
| 8,021,424 B2 | 9/2011 | Beger et al. | |
| 8,021,426 B2 | 9/2011 | Segal et al. | |
| 8,062,365 B2 | 11/2011 | Schwab | |
| 8,092,536 B2 | 1/2012 | Ahrens et al. | |
| 8,142,507 B2 | 3/2012 | McGuckin, Jr. | |
| 8,152,849 B2 | 4/2012 | Biedermann et al. | |
| 8,182,538 B2 | 5/2012 | O'Neil et al. | |
| 8,226,718 B2 | 7/2012 | Castro | |
| 8,241,363 B2 | 8/2012 | Sommerich et al. | |
| 8,246,683 B2 | 8/2012 | Castro | |
| 8,252,059 B2 | 8/2012 | Overes et al. | |
| 8,298,286 B2 | 10/2012 | Trieu | |
| 8,303,879 B2 | 11/2012 | Bertele et al. | |
| 8,343,224 B2 | 1/2013 | Lynn | |
| 8,361,149 B2 | 1/2013 | Castro | |
| 8,366,777 B2 | 2/2013 | Matthis et al. | |
| D681,204 S | 4/2013 | Farris et al. | |
| 8,414,654 B1 | 4/2013 | Ganey | |
| 8,414,820 B2 | 4/2013 | Bertele et al. | |
| 8,430,930 B2 * | 4/2013 | Hunt ..................... | A61B 17/56 623/17.11 |
| D681,812 S | 5/2013 | Farris et al. | |
| 8,435,300 B2 | 5/2013 | Messerli et al. | |
| 8,454,700 B2 | 6/2013 | Lemoine et al. | |
| 8,475,533 B1 | 7/2013 | Castro | |
| 8,529,628 B2 | 9/2013 | Marino et al. | |
| 8,551,173 B2 | 10/2013 | Lechmann et al. | |
| 8,556,978 B2 | 10/2013 | Schaller | |
| 8,568,413 B2 | 10/2013 | Mazur et al. | |
| 8,613,769 B2 | 12/2013 | Sears et al. | |
| 8,623,090 B2 | 1/2014 | Butler | |
| 8,673,006 B2 | 3/2014 | Castro | |
| 8,700,198 B2 | 4/2014 | Conway et al. | |
| 8,702,808 B2 | 4/2014 | Teoh et al. | |
| 8,709,042 B2 | 4/2014 | Greenhalgh et al. | |
| 8,728,160 B2 | 5/2014 | Globerman | |
| 8,740,981 B2 | 6/2014 | Tornier et al. | |

(56) References Cited

U.S. PATENT DOCUMENTS

| | | |
|---|---|---|
| 8,771,357 B2 | 7/2014 | Biedermann et al. |
| 8,771,368 B2 | 7/2014 | McKay |
| 8,795,362 B2 | 8/2014 | Anderson et al. |
| 8,801,787 B2 | 8/2014 | Schaller |
| 8,808,376 B2 | 8/2014 | Schaller |
| 8,808,725 B2 | 8/2014 | Altschuler et al. |
| 8,840,614 B2 | 9/2014 | Mikhail et al. |
| 8,864,831 B2 | 10/2014 | Lee et al. |
| 8,894,661 B2 | 11/2014 | McDevitt |
| 8,900,310 B2 | 12/2014 | Carlson |
| 8,900,312 B2 | 12/2014 | McLean et al. |
| 8,932,356 B2 | 1/2015 | Kraus |
| 8,940,050 B2 | 1/2015 | Laurence |
| 8,940,052 B2 | 1/2015 | Lechmann et al. |
| 8,951,300 B2 | 2/2015 | Parrish |
| 8,986,383 B2 | 3/2015 | Castro |
| 9,011,499 B1 | 4/2015 | Kiester |
| 9,039,766 B1 | 5/2015 | Fonte |
| 9,060,876 B1 | 6/2015 | To |
| 9,101,491 B2 | 8/2015 | Rodgers |
| D739,935 S | 9/2015 | Blain et al. |
| 9,138,301 B2 | 9/2015 | Kita et al. |
| 9,155,819 B2 | 10/2015 | Fonte et al. |
| 9,186,252 B2 | 11/2015 | Leibinger |
| 9,186,257 B2 | 11/2015 | Geisler |
| 9,220,518 B2 | 12/2015 | Neal et al. |
| 9,237,958 B2 | 1/2016 | Duggal et al. |
| 9,247,970 B2 | 2/2016 | Teisen |
| 9,254,199 B2 | 2/2016 | Biedermann et al. |
| 9,271,765 B2 | 3/2016 | Blain |
| 9,271,771 B2 | 3/2016 | Mathieu et al. |
| 9,271,845 B2 | 3/2016 | Hunt et al. |
| 9,289,308 B2 | 3/2016 | Marino et al. |
| 9,289,312 B2 | 3/2016 | Davenport et al. |
| 9,295,562 B2 | 3/2016 | Lechmann et al. |
| 9,364,233 B2 | 6/2016 | Lindsey et al. |
| 9,364,339 B2 | 6/2016 | Mayer |
| 9,402,733 B1 | 8/2016 | To et al. |
| 9,408,651 B2 | 8/2016 | Sennett et al. |
| 9,421,108 B2 | 8/2016 | Hunt |
| 9,427,328 B2 | 8/2016 | Drochner |
| 9,433,510 B2 | 9/2016 | Lechmann et al. |
| 9,433,511 B2 | 9/2016 | Bagga et al. |
| 9,439,779 B2 | 9/2016 | Zhang et al. |
| 9,439,948 B2 | 9/2016 | Lin et al. |
| 9,452,056 B2 | 9/2016 | Early et al. |
| 9,452,064 B2 | 9/2016 | Trautwein et al. |
| 9,456,901 B2 | 10/2016 | Jones et al. |
| 9,456,907 B1 | 10/2016 | Castro |
| 9,517,095 B2 | 12/2016 | Vaidya |
| 9,522,028 B2 | 12/2016 | Warren et al. |
| 9,526,548 B2 | 12/2016 | Asfora |
| 9,545,317 B2 | 1/2017 | Hunt |
| 9,549,823 B2 | 1/2017 | Hunt et al. |
| 9,554,914 B2 | 1/2017 | Taylor et al. |
| 9,561,117 B2 | 2/2017 | Lechmann et al. |
| 9,566,095 B2 | 2/2017 | Lorio |
| 9,566,100 B2 | 2/2017 | Asfora |
| 9,572,669 B2 | 2/2017 | Hunt et al. |
| 9,597,197 B2 | 3/2017 | Lechmann et al. |
| 9,603,613 B2 | 3/2017 | Schoenefeld et al. |
| 9,622,880 B2 | 4/2017 | Dunworth et al. |
| 9,629,727 B2 | 4/2017 | Baynham |
| 9,636,226 B2 | 5/2017 | Hunt |
| 9,649,200 B2 | 5/2017 | Wickham |
| 9,662,128 B2 | 5/2017 | Reiley |
| 9,662,157 B2 | 5/2017 | Schneider et al. |
| 9,662,158 B2 | 5/2017 | Reiley |
| 9,662,224 B2 | 5/2017 | Weiman et al. |
| 9,662,226 B2 | 5/2017 | Wickham |
| 9,668,781 B2 | 6/2017 | Stark |
| 9,675,394 B2 | 6/2017 | Reiley |
| 9,700,356 B2 | 7/2017 | Donner et al. |
| 9,744,051 B2 | 8/2017 | Biedermann et al. |
| 9,757,235 B2 | 9/2017 | Hunt et al. |
| 9,782,270 B2 | 10/2017 | Wickham |
| 9,788,967 B2 | 10/2017 | Jo |
| 9,814,578 B1 | 11/2017 | Gotfried |
| 9,907,670 B2 | 3/2018 | DeRidder et al. |
| 9,918,849 B2* | 3/2018 | Morris ............... A61F 2/30744 |
| 9,931,209 B2 | 4/2018 | Gotfried |
| 9,987,051 B2 | 6/2018 | Nunley et al. |
| 9,987,137 B2 | 6/2018 | Hunt et al. |
| 9,999,516 B2 | 6/2018 | Hunt |
| 10,004,546 B2 | 6/2018 | Gotfried |
| 10,016,279 B1 | 7/2018 | Castro |
| 10,058,433 B2 | 8/2018 | Lechmann et al. |
| 10,064,737 B2 | 9/2018 | Tsai et al. |
| 10,098,754 B2 | 10/2018 | Larsson |
| 10,117,746 B2 | 11/2018 | Cordaro |
| 10,143,569 B2 | 12/2018 | Weiman et al. |
| 10,154,913 B2 | 12/2018 | Steinmann et al. |
| 10,159,580 B2 | 12/2018 | Guizzardi et al. |
| 10,182,923 B2 | 1/2019 | Willis et al. |
| 10,194,962 B2 | 2/2019 | Schneider et al. |
| 10,195,524 B2 | 2/2019 | DeRidder et al. |
| 10,213,317 B2 | 2/2019 | Bishop et al. |
| 10,226,357 B2 | 3/2019 | Ries |
| 10,265,189 B2 | 4/2019 | Melkent et al. |
| 10,271,958 B2 | 4/2019 | Schaufler et al. |
| 10,278,833 B2 | 5/2019 | Howard et al. |
| 10,278,834 B2 | 5/2019 | Howard et al. |
| 10,357,377 B2 | 7/2019 | Nyahay et al. |
| 10,368,997 B2 | 8/2019 | Jones et al. |
| 10,369,009 B2 | 8/2019 | Joly et al. |
| 10,413,427 B2 | 9/2019 | Trieu |
| 10,433,977 B2 | 10/2019 | Lechmann et al. |
| 10,433,979 B2 | 10/2019 | Morris et al. |
| 10,449,051 B2 | 10/2019 | Hamzey et al. |
| 10,449,055 B2 | 10/2019 | McJunkin |
| 10,449,058 B2 | 10/2019 | Lechmann et al. |
| 10,478,312 B2 | 11/2019 | McShane, III et al. |
| D870,288 S | 12/2019 | Dang et al. |
| 10,492,921 B2 | 12/2019 | McShane, III et al. |
| 10,507,118 B2 | 12/2019 | Afzal |
| 10,512,549 B2* | 12/2019 | Bishop ............... A61F 2/447 |
| 10,517,739 B2 | 12/2019 | Ryan |
| 10,524,926 B2 | 1/2020 | Jasinski |
| 10,524,927 B2 | 1/2020 | Ryan |
| 10,524,929 B2 | 1/2020 | Shoshtaev |
| 10,525,688 B2 | 1/2020 | O'Neill et al. |
| 10,531,962 B2 | 1/2020 | Petersheim et al. |
| 10,537,666 B2 | 1/2020 | Paddock et al. |
| 10,555,819 B2 | 2/2020 | Miccio |
| 10,561,456 B2 | 2/2020 | Cawley et al. |
| 10,575,965 B2 | 3/2020 | Kim et al. |
| 10,588,755 B2 | 3/2020 | Vogt et al. |
| 10,617,532 B2 | 4/2020 | Mazur et al. |
| 10,624,760 B2 | 4/2020 | Mirda et al. |
| 10,660,763 B2 | 5/2020 | Wilson et al. |
| 10,660,764 B2 | 5/2020 | Maglaras et al. |
| 10,667,924 B2 | 6/2020 | Nyahay et al. |
| 10,675,158 B2 | 6/2020 | Unger et al. |
| 10,675,385 B2 | 6/2020 | Barbas et al. |
| 10,682,238 B2 | 6/2020 | Petersheim et al. |
| 10,695,192 B2 | 6/2020 | Bishop et al. |
| 10,709,570 B2 | 7/2020 | Stauffer et al. |
| 10,716,678 B2 | 7/2020 | Stampfli et al. |
| 10,722,378 B2 | 7/2020 | Davis et al. |
| 10,744,001 B2 | 8/2020 | Sack |
| 10,744,003 B2 | 8/2020 | Ryan et al. |
| 10,765,530 B2 | 9/2020 | Steinmann et al. |
| 10,772,732 B1 | 9/2020 | Miller et al. |
| D898,197 S | 10/2020 | Cain |
| 10,835,388 B2 | 11/2020 | Milz et al. |
| 10,849,756 B2 | 12/2020 | Hunt et al. |
| 10,856,999 B2 | 12/2020 | Bishop et al. |
| 10,940,019 B2 | 3/2021 | Vishnubhotla et al. |
| D920,515 S | 5/2021 | Miller et al. |
| D920,516 S | 5/2021 | Miller et al. |
| 11,026,798 B1 | 6/2021 | Miller et al. |
| 11,033,394 B2 | 6/2021 | Hamzey et al. |
| 11,065,039 B2 | 7/2021 | McCormack |
| 11,147,679 B2 | 10/2021 | Kowalczyk et al. |

(56) References Cited

U.S. PATENT DOCUMENTS

| | | |
|---|---|---|
| 11,160,668 B2 | 11/2021 | Nyahay et al. |
| D942,011 S | 1/2022 | Cain |
| 11,213,405 B2* | 1/2022 | Bishop .................. A61F 2/4455 |
| D942,623 S | 2/2022 | Cain |
| D942,624 S | 2/2022 | Cain |
| D944,400 S | 2/2022 | Cain |
| 11,273,048 B2 | 3/2022 | Cain et al. |
| 11,452,611 B2 | 9/2022 | McShane, III et al. |
| 2001/0014826 A1 | 8/2001 | Biedermann et al. |
| 2001/0032018 A1 | 10/2001 | Castro et al. |
| 2002/0052656 A1 | 5/2002 | Michelson |
| 2002/0120334 A1 | 8/2002 | Crozet |
| 2002/0123750 A1 | 9/2002 | Eisermann et al. |
| 2002/0183847 A1 | 12/2002 | Lieberman |
| 2003/0003127 A1 | 1/2003 | Brown et al. |
| 2003/0060825 A1 | 3/2003 | Alfaro |
| 2003/0078660 A1 | 4/2003 | Clifford et al. |
| 2003/0083746 A1 | 5/2003 | Kuslich |
| 2003/0109928 A1 | 6/2003 | Pasquet |
| 2003/0181913 A1 | 9/2003 | Lieberman |
| 2003/0236571 A1 | 12/2003 | Ralph |
| 2004/0059419 A1 | 3/2004 | Michelson |
| 2004/0082953 A1 | 4/2004 | Petit |
| 2004/0122518 A1 | 6/2004 | Rhoda |
| 2004/0193270 A1 | 9/2004 | DiMauro et al. |
| 2004/0210312 A1 | 10/2004 | Neumann |
| 2004/0225361 A1 | 11/2004 | Glenn et al. |
| 2004/0243129 A1* | 12/2004 | Moumene .......... A61B 17/8625 606/315 |
| 2005/0015154 A1 | 1/2005 | Lindsey et al. |
| 2005/0027364 A1 | 2/2005 | Kim |
| 2005/0143733 A1 | 6/2005 | Petit |
| 2005/0177238 A1 | 8/2005 | Khandkar et al. |
| 2005/0187627 A1* | 8/2005 | Ralph .................... A61F 2/4611 623/17.11 |
| 2005/0222681 A1 | 10/2005 | Richley et al. |
| 2005/0278027 A1 | 12/2005 | Hyde, Jr. |
| 2005/0278028 A1 | 12/2005 | Mujwid |
| 2006/0041262 A1 | 2/2006 | Calvert et al. |
| 2006/0052872 A1 | 3/2006 | Studer |
| 2006/0052873 A1 | 3/2006 | Buck |
| 2006/0058881 A1 | 3/2006 | Trieu |
| 2006/0100706 A1 | 5/2006 | Shadduck et al. |
| 2006/0147332 A1 | 7/2006 | Jones et al. |
| 2006/0212118 A1 | 9/2006 | Abernathie |
| 2006/0217806 A1 | 9/2006 | Peterman |
| 2006/0293753 A1 | 12/2006 | Thramann |
| 2007/0027544 A1 | 2/2007 | McCord et al. |
| 2007/0179610 A1 | 8/2007 | Biedermann et al. |
| 2007/0198090 A1 | 8/2007 | Abdou |
| 2007/0260324 A1 | 11/2007 | Joshi et al. |
| 2008/0071356 A1 | 3/2008 | Greenhalgh |
| 2008/0167686 A1 | 7/2008 | Trieu |
| 2008/0183204 A1 | 7/2008 | Greenhalgh et al. |
| 2008/0255666 A1 | 10/2008 | Fisher |
| 2008/0288083 A1 | 11/2008 | Axelsson et al. |
| 2008/0300602 A1 | 12/2008 | Schmitt et al. |
| 2008/0306595 A1 | 12/2008 | McLeod et al. |
| 2008/0312742 A1 | 12/2008 | Abernathie |
| 2009/0030520 A1 | 1/2009 | Biedermann |
| 2009/0036985 A1 | 2/2009 | Whiting |
| 2009/0048675 A1 | 2/2009 | Bhatnagar et al. |
| 2009/0048678 A1 | 2/2009 | Saal et al. |
| 2009/0062917 A1 | 3/2009 | Foley et al. |
| 2009/0112321 A1* | 4/2009 | Kitchen .................... C22F 1/10 623/17.11 |
| 2009/0149958 A1 | 6/2009 | Prewett et al. |
| 2009/0248162 A1 | 10/2009 | Peckham |
| 2010/0016974 A1 | 1/2010 | Janowski |
| 2010/0036498 A1 | 2/2010 | McDevitt |
| 2010/0057216 A1 | 3/2010 | Gannoe et al. |
| 2010/0137990 A1 | 6/2010 | Apatsidis |
| 2010/0152856 A1 | 6/2010 | Overes |
| 2010/0161061 A1 | 6/2010 | Hunt |
| 2010/0185292 A1 | 7/2010 | Hochschuler |
| 2010/0228299 A1 | 9/2010 | Zrinski et al. |
| 2010/0286778 A1 | 11/2010 | Eisermann et al. |
| 2011/0015741 A1 | 1/2011 | Melkent et al. |
| 2011/0029085 A1 | 2/2011 | Hynes |
| 2011/0035019 A1 | 2/2011 | Goswami et al. |
| 2011/0066192 A1 | 3/2011 | Frasier et al. |
| 2011/0166660 A1* | 7/2011 | Laurence ................ A61F 2/442 623/17.16 |
| 2011/0190888 A1 | 8/2011 | Bertele |
| 2011/0190895 A1 | 8/2011 | Segal et al. |
| 2011/0208311 A1 | 8/2011 | Janowski |
| 2011/0230970 A1 | 9/2011 | Lynn |
| 2011/0245926 A1 | 10/2011 | Kitchen |
| 2011/0270401 A1 | 11/2011 | McKay |
| 2011/0301709 A1 | 12/2011 | Kraus et al. |
| 2011/0313528 A1 | 12/2011 | Laubert |
| 2011/0313532 A1* | 12/2011 | Hunt ........................ A61F 2/46 623/18.11 |
| 2012/0010472 A1 | 1/2012 | Spann |
| 2012/0010717 A1 | 1/2012 | Spann |
| 2012/0150300 A1 | 6/2012 | Nihalani |
| 2012/0158143 A1 | 6/2012 | Shapiro |
| 2012/0191188 A1 | 7/2012 | Huang |
| 2012/0191189 A1 | 7/2012 | Huang |
| 2012/0239150 A1 | 9/2012 | Ullrich |
| 2012/0296431 A1 | 11/2012 | Kim |
| 2013/0030529 A1* | 1/2013 | Hunt .................. A61F 2/30771 623/16.11 |
| 2013/0096685 A1 | 4/2013 | Ciupik |
| 2013/0116793 A1* | 5/2013 | Kloss ...................... A61F 2/442 623/17.16 |
| 2013/0123935 A1 | 5/2013 | Hunt et al. |
| 2013/0158672 A1 | 6/2013 | Hunt |
| 2013/0184826 A1 | 7/2013 | Thaiyananthan |
| 2013/0190880 A1 | 7/2013 | Schaller |
| 2013/0021288 A1 | 8/2013 | Fonte |
| 2013/0204374 A1* | 8/2013 | Milella, Jr. ............ A61F 2/4611 623/17.16 |
| 2013/0218282 A1* | 8/2013 | Hunt ........................ A61F 2/447 623/23.42 |
| 2013/0218288 A1 | 8/2013 | Fonte |
| 2013/0226300 A1 | 8/2013 | Chataigner |
| 2013/0304211 A1 | 11/2013 | Trautwein et al. |
| 2013/0325129 A1* | 12/2013 | Huang ...................... A61F 2/44 623/17.16 |
| 2014/0018814 A1 | 1/2014 | Gillard et al. |
| 2014/0052260 A1 | 2/2014 | McKenny |
| 2014/0058513 A1 | 2/2014 | Gahman et al. |
| 2014/0107785 A1 | 4/2014 | Geisler |
| 2014/0107786 A1* | 4/2014 | Geisler .................... A61F 2/447 623/17.16 |
| 2014/0114418 A1 | 4/2014 | Landry |
| 2014/0121776 A1* | 5/2014 | Hunt .................. A61F 2/30942 623/17.16 |
| 2014/0142707 A1 | 5/2014 | Compton et al. |
| 2014/0172111 A1 | 6/2014 | Lang et al. |
| 2014/0195005 A1 | 7/2014 | McKay |
| 2014/0228956 A1 | 8/2014 | Weiman |
| 2014/0228960 A1 | 8/2014 | Forterre |
| 2014/0243980 A1 | 8/2014 | Sack et al. |
| 2014/0249631 A1 | 9/2014 | Weiman |
| 2014/0277457 A1 | 9/2014 | Yeung et al. |
| 2014/0277464 A1 | 9/2014 | Richter et al. |
| 2014/0277569 A1 | 9/2014 | Lange |
| 2014/0288649 A1* | 9/2014 | Hunt ........................ A61F 2/447 623/16.11 |
| 2014/0288650 A1* | 9/2014 | Hunt ........................ A61F 2/447 623/16.11 |
| 2014/0303736 A1 | 10/2014 | Roussouly |
| 2014/0303745 A1 | 10/2014 | Anderson et al. |
| 2014/0309743 A1 | 10/2014 | Falahee |
| 2014/0336771 A1 | 11/2014 | Zambiasi |
| 2014/0358246 A1 | 12/2014 | Levy et al. |
| 2015/0045903 A1 | 2/2015 | Neal |
| 2015/0112351 A1 | 4/2015 | Hsu |
| 2015/0127106 A1* | 5/2015 | Partee ................ A61L 27/3616 623/17.11 |
| 2015/0173910 A1 | 6/2015 | Siegal |

(56) References Cited

U.S. PATENT DOCUMENTS

| | | |
|---|---|---|
| 2015/0223951 A1 | 8/2015 | Bae et al. |
| 2015/0282944 A1 | 10/2015 | Guizzardi et al. |
| 2015/0359635 A1 | 12/2015 | Kita et al. |
| 2016/0015437 A1 | 1/2016 | Elleby et al. |
| 2016/0022430 A1 | 1/2016 | Wickham |
| 2016/0081809 A1 | 3/2016 | Schneider et al. |
| 2016/0166284 A1 | 6/2016 | Hacking et al. |
| 2016/0184103 A1 | 6/2016 | Fonte et al. |
| 2016/0193057 A1 | 7/2016 | Rhoda |
| 2016/0206439 A1 | 7/2016 | To et al. |
| 2016/0206440 A1 | 7/2016 | DeRidder et al. |
| 2016/0262903 A1 | 9/2016 | West |
| 2016/0270920 A1 | 9/2016 | Dawson et al. |
| 2016/0287388 A1 | 10/2016 | Hunt et al. |
| 2016/0310294 A1 | 10/2016 | McConnell et al. |
| 2016/0317320 A1 | 11/2016 | Ahn |
| 2016/0324656 A1* | 11/2016 | Morris ............... A61F 2/30744 |
| 2016/0374727 A1 | 12/2016 | Greenhalgh et al. |
| 2017/0007409 A1 | 1/2017 | Mauldin et al. |
| 2017/0014235 A1 | 1/2017 | Jones et al. |
| 2017/0020685 A1 | 1/2017 | Geisler et al. |
| 2017/0042697 A1* | 2/2017 | McShane, III ........ A61F 2/4455 |
| 2017/0049488 A1 | 2/2017 | Vestgaarden |
| 2017/0095337 A1 | 4/2017 | Pasini et al. |
| 2017/0095352 A1 | 4/2017 | Bruffey |
| 2017/0100167 A1 | 4/2017 | Lange et al. |
| 2017/0135706 A1 | 5/2017 | Frey et al. |
| 2017/0135733 A1 | 5/2017 | Donner et al. |
| 2017/0143383 A1 | 5/2017 | Ingalhalikar et al. |
| 2017/0151005 A1 | 6/2017 | Warren et al. |
| 2017/0156740 A9 | 6/2017 | Stark |
| 2017/0156766 A1 | 6/2017 | Anderson et al. |
| 2017/0156878 A1 | 6/2017 | Tsai |
| 2017/0156879 A1* | 6/2017 | Janowski .............. A61F 2/4611 |
| 2017/0156880 A1 | 6/2017 | Halverson et al. |
| 2017/0164979 A1 | 6/2017 | Donner et al. |
| 2017/0181784 A1 | 6/2017 | Li |
| 2017/0182222 A1 | 6/2017 | Paddock |
| 2017/0196693 A1 | 7/2017 | Jurick et al. |
| 2017/0216034 A1* | 8/2017 | Daniel .................. A61F 2/2846 |
| 2017/0216035 A1 | 8/2017 | Hunt |
| 2017/0239064 A1 | 8/2017 | Cordaro |
| 2017/0239066 A1 | 8/2017 | Walsh et al. |
| 2017/0258606 A1 | 9/2017 | Afzal |
| 2017/0319353 A1 | 11/2017 | Greenhalgh et al. |
| 2017/0348107 A1 | 12/2017 | Lee et al. |
| 2017/0348115 A1 | 12/2017 | Greenhalgh |
| 2018/0064540 A1 | 3/2018 | Hunt et al. |
| 2018/0085230 A1 | 3/2018 | Hunt |
| 2018/0110626 A1 | 4/2018 | McShane, III |
| 2018/0161477 A1 | 6/2018 | Nies |
| 2018/0221156 A1 | 8/2018 | Jones |
| 2018/0243104 A1 | 8/2018 | Garonzik |
| 2018/0256336 A1 | 9/2018 | Mueller et al. |
| 2018/0256351 A1* | 9/2018 | Bishop .................. A61F 2/4455 |
| 2018/0256352 A1* | 9/2018 | Nyahay ................ A61F 2/4455 |
| 2018/0256353 A1* | 9/2018 | Nyahay ................ A61F 2/4455 |
| 2018/0280139 A1 | 10/2018 | Jones |
| 2018/0289503 A1 | 10/2018 | Knapp |
| 2018/0296343 A1 | 10/2018 | Wei |
| 2018/0296347 A1* | 10/2018 | Hamzey ............. A61B 17/8095 |
| 2018/0326493 A1 | 11/2018 | Gallagher et al. |
| 2018/0333272 A1 | 11/2018 | Mirda |
| 2018/0338838 A1* | 11/2018 | Cryder ............... A61B 17/8811 |
| 2018/0368981 A1 | 12/2018 | Mattes et al. |
| 2018/0368991 A1 | 12/2018 | Levieux |
| 2019/0000636 A1 | 1/2019 | Kim et al. |
| 2019/0015209 A1 | 1/2019 | Seifert et al. |
| 2019/0038428 A1 | 2/2019 | Stauffer |
| 2019/0060079 A1 | 2/2019 | Unis et al. |
| 2019/0060083 A1 | 2/2019 | Weiman et al. |
| 2019/0076266 A1 | 3/2019 | Trudeau et al. |
| 2019/0083282 A1 | 3/2019 | Roeder et al. |
| 2019/0091027 A1 | 3/2019 | Asaad et al. |
| 2019/0133769 A1 | 5/2019 | Tetsworth et al. |
| 2019/0151109 A1 | 5/2019 | Amin |
| 2019/0151113 A1 | 5/2019 | Sack |
| 2019/0159818 A1 | 5/2019 | Schneider et al. |
| 2019/0183653 A1 | 6/2019 | Gregersen et al. |
| 2019/0224023 A1 | 7/2019 | Howard et al. |
| 2019/0254840 A1 | 8/2019 | Gray et al. |
| 2019/0262139 A1 | 8/2019 | Wolters |
| 2019/0274841 A1 | 9/2019 | Hawkes et al. |
| 2019/0298542 A1 | 10/2019 | Kloss |
| 2019/0307574 A1 | 10/2019 | Nyahay et al. |
| 2019/0314169 A1 | 10/2019 | Patel et al. |
| 2019/0328546 A1 | 10/2019 | Palagi et al. |
| 2019/0336305 A1 | 11/2019 | Joly et al. |
| 2019/0343645 A1 | 11/2019 | Miccio et al. |
| 2019/0358058 A1 | 11/2019 | Trieu |
| 2019/0388238 A1 | 12/2019 | Lechmann et al. |
| 2020/0000603 A1 | 1/2020 | McJunkin |
| 2020/0036011 A1 | 1/2020 | Numata et al. |
| 2020/0038197 A1 | 2/2020 | Morris et al. |
| 2020/0038198 A1 | 2/2020 | Miccio |
| 2020/0086625 A1 | 3/2020 | O'Neill et al. |
| 2020/0113707 A1 | 4/2020 | Petersheim et al. |
| 2020/0113709 A1 | 4/2020 | Hsieh |
| 2020/0121470 A1 | 4/2020 | Moore et al. |
| 2020/0138595 A1 | 5/2020 | Shoshtaev et al. |
| 2020/0146842 A1 | 5/2020 | Jasinski |
| 2020/0155326 A1 | 5/2020 | Hunt |
| 2020/0179128 A1 | 6/2020 | Stalcup et al. |
| 2020/0179133 A1 | 6/2020 | Ryan |
| 2020/0188120 A1 | 6/2020 | Hamzey et al. |
| 2020/0188129 A1 | 6/2020 | McShane, III et al. |
| 2020/0188132 A1 | 6/2020 | Ryan |
| 2020/0188133 A1 | 6/2020 | McShane, III et al. |
| 2020/0190680 A1 | 6/2020 | Numata et al. |
| 2020/0197189 A1 | 6/2020 | Mazur et al. |
| 2020/0214852 A1 | 7/2020 | Tipping et al. |
| 2020/0222201 A1 | 7/2020 | Mirda et al. |
| 2020/0229940 A1* | 7/2020 | Bishop .................. A61F 2/4455 |
| 2020/0229945 A1 | 7/2020 | Levieux |
| 2020/0237526 A1 | 7/2020 | Wilson et al. |
| 2020/0246160 A1 | 8/2020 | Zappacosta et al. |
| 2020/0261243 A1 | 8/2020 | Unger et al. |
| 2020/0268523 A1 | 8/2020 | Barthold et al. |
| 2020/0276019 A1 | 9/2020 | Shetty et al. |
| 2020/0281727 A1 | 9/2020 | Dang et al. |
| 2020/0297494 A1 | 9/2020 | Hunt et al. |
| 2020/0297505 A1 | 9/2020 | McLaughlin |
| 2020/0315812 A1 | 10/2020 | Davis et al. |
| 2020/0323645 A1 | 10/2020 | Northcutt et al. |
| 2020/0337851 A1 | 10/2020 | Stampfli et al. |
| 2020/0337855 A1 | 10/2020 | Stauffer et al. |
| 2020/0337856 A1 | 10/2020 | Moore et al. |
| 2020/0345506 A1 | 11/2020 | Rayan et al. |
| 2020/0352735 A1 | 11/2020 | Afzal |
| 2020/0375757 A1 | 12/2020 | Sack |
| 2020/0375758 A1 | 12/2020 | Northcutt et al. |
| 2020/0376174 A1 | 12/2020 | Melkent et al. |
| 2021/0022882 A1 | 1/2021 | Dang et al. |
| 2021/0046211 A1 | 2/2021 | Deisinger et al. |
| 2021/0069383 A1 | 3/2021 | Yamaguchi et al. |
| 2021/0085481 A1 | 3/2021 | Cain et al. |
| 2021/0307909 A1 | 10/2021 | Hamzey et al. |
| 2022/0047398 A1 | 2/2022 | Nyahay et al. |
| 2022/0071777 A1 | 3/2022 | Cain et al. |
| 2022/0117751 A1* | 4/2022 | Bishop .................. A61F 2/4455 |
| 2022/0117753 A1 | 4/2022 | Rucker et al. |

FOREIGN PATENT DOCUMENTS

| | | |
|---|---|---|
| CN | 204931903 | 1/2016 |
| CN | 110179570 B | 8/2021 |
| DE | 19722389 | 12/1998 |
| EP | 3064175 | 9/2016 |
| EP | 3494931 | 6/2019 |
| EP | 3517078 | 7/2019 |
| EP | 3603580 | 2/2020 |
| FR | 2815846 | 5/2002 |
| FR | 2955025 | 7/2011 |
| JP | H05261146 | 10/1993 |

(56) References Cited

FOREIGN PATENT DOCUMENTS

| | | |
|---|---|---|
| JP | H09503416 | 9/1997 |
| JP | 2001523129 | 11/2001 |
| JP | 20010523129 | 11/2001 |
| JP | 2004-510494 | 4/2004 |
| JP | 2006515194 | 5/2006 |
| JP | 2007151805 | 6/2007 |
| JP | 2009-505686 | 2/2009 |
| JP | 2009504332 | 2/2009 |
| JP | 4313005 | 8/2009 |
| JP | 2010137069 | 6/2010 |
| JP | 201115959 | 1/2011 |
| JP | 2011015959 | 1/2011 |
| JP | 2012-501236 | 1/2012 |
| JP | 2012501236 | 1/2012 |
| JP | 20120501236 | 1/2012 |
| JP | 5328051 | 10/2013 |
| JP | 5455020 | 3/2014 |
| JP | 2014-151209 | 8/2014 |
| JP | 2015-502192 | 1/2015 |
| JP | 2015502192 | 1/2015 |
| JP | 5684177 | 3/2015 |
| JP | 2015529150 | 10/2015 |
| JP | A2018-516646 | 6/2018 |
| JP | 2019034071 | 3/2019 |
| JP | 2019041886 | 3/2019 |
| JP | 2019180797 | 10/2019 |
| JP | 2019201688 | 11/2019 |
| JP | 6700135 | 5/2020 |
| JP | 2020199326 | 12/2020 |
| JP | 2021016498 | 2/2021 |
| PA | 2012-501236 | 1/2012 |
| WO | WO 9510248 | 4/1995 |
| WO | WO 9848738 | 11/1998 |
| WO | WO 9852498 | 11/1998 |
| WO | WO 0209625 | 2/2002 |
| WO | WO 0234168 | 5/2002 |
| WO | WO 03099160 | 12/2003 |
| WO | WO 2004084774 | 10/2004 |
| WO | WO 2005011523 | 2/2005 |
| WO | WO 2009051779 | 3/2006 |
| WO | WO 2007022194 | 2/2007 |
| WO | WO 2009051779 | 4/2009 |
| WO | WO 2010028056 | 3/2010 |
| WO | WO 2010097632 | 9/2010 |
| WO | WO 2013067528 | 5/2013 |
| WO | WO 2014052477 | 4/2014 |
| WO | 2014168631 | 10/2014 |
| WO | WO 2016044739 | 3/2016 |
| WO | WO 2016176496 | 11/2016 |
| WO | WO 2017100366 | 6/2017 |

OTHER PUBLICATIONS

Office Action dated Nov. 1, 2018 in U.S. Appl. No. 15/885,418.
Final Office Action dated Feb. 25, 2019 in U.S. Appl. No. 15/885,418.
Office Action dated Nov. 2, 2021 in U.S. Appl. No. 16/593,101.
International Search Report and Written Opinion dated Aug. 19, 2016 in PCT/US2016/029865.
Office Action dated Apr. 3, 2019 in Chinese Application No. 2016800391036.
Office Action dated Jun. 28, 2019 in European Application No. 16722008.6-1132.
Extended European Search Report dated Dec. 8, 2020 in European Application No. 20191843.0-1132.
ISO/ASTM 52900:2015€ Standard Terminology for Additive Manufacturing—General Principles—Terminology, 2017.
Office Action dated Mar. 5, 2020 in Japanese Application No. 2017-556733.
Office Action dated Sep. 2, 2021 in Japanese Application No. 2020-156918.
Notice of Decision to Grant a Patent dated Jul. 7, 2022 in Japanese Application No. 2020-156918.
Office Action dated Sep. 2, 2021 in Japanese Application No. 2020-156917.
Notice of Decision to Grant a Patent dated Jul. 7, 2022 in Japanese Application No. 2020-156917.
Office Action dated May 2, 2018 in U.S. Appl. No. 15/334,975.
Office Action dated Dec. 3, 2018 in U.S. Appl. No. 15/334,053.
Office Action dated Sep. 15, 2022 in U.S. Appl. No. 16/700,632.
Final Office Action dated Jun. 2, 2023 in U.S. Appl. No. 16/700,632.
International Search Report and Written Opinion dated Jan. 18, 2018.
"FDA Clears Camber Spine Technologies' 3D Printed SPIRA Open Matrix ALIF", Orthopedic Design & Technology, Aug. 15, 2017.
Supplemental Partial European Search Report dated May 15, 2020 in European Application No. 17866284.
Office Action dated Sep. 3, 2020 in European Application No. 17866284.
Office Action dated Mar. 23, 2022 in Chinese Application No. 2017800805197.
Office Action dated Mar. 25, 2021 in Japanese Application No. 2019-543187.
Office Action dated Aug. 5, 2021 in Japanese Application No. 2019-543187.
Office Action dated Jan. 12, 2022 in Japanese Application No. 2019-543187.
Preliminary Office Action dated Jan. 24, 2022 in Brazilian Application No. 112019008325-1.
Office Action dated Feb. 16, 2023 in Japanese Application No. 2021-197842.
Office Action dated Jul. 8, 2019 in U.S. Appl. No. 15/884,845.
Final Office Action dated Oct. 24, 2019 in U.S. Appl. No. 15/884,845.
International Search Report and Written Opinion dated Apr. 26, 2019 in PCT/US19/15946.
Office Action dated Dec. 9, 2021 in Japanese Application No. 2020-540800.
Office Action dated Apr. 27, 2023 in Japanese Application No. 2022-086976.
Office Action dated Nov. 5, 2020 in Australian Application No. 2019214987.
Office Action dated Oct. 15, 2021 in Australian Application No. 2019214987.
Office Action dated Mar. 27, 2023 in Australian Application No. 2022200666.
Office Action dated Oct. 25, 2018 in U.S. Appl. No. 15/791,279.
Final Office Action dated Mar. 1, 2019 in U.S. Appl. No. 15/791,279.
Office Action dated Mar. 1, 2022 in U.S. Appl. No. 16/659,011.
Final Office Action dated Jun. 21, 2022 in U.S. Appl. No. 16/659,011.
Office Action dated Feb. 27, 2023 in U.S. Appl. No. 16/659,011.
Office Action dated Apr. 20, 2023 in JP Application No. 2022-124717.
Notice of Allowance dated Dec. 4, 2023 in U.S. Application No.
Office Action dated Nov. 30, 2023 in Japanese Application No. 2021-197842.
Notice of Allowance dated Jan. 18, 2024 in Japanese Application No. 2022-086976.
Jan. 11, 2024 in JP Application No. 2021-166902.
Office Action dated Dec. 12, 2023 in European Application No. 17866273.0-1122.

* cited by examiner

IMPLANT WITH STRUCTURAL MEMBERS ARRANGED AROUND A RING

CROSS-REFERENCE TO RELATED APPLICATIONS

This application is a continuation of Bishop et al., U.S. Patent Application Publ. No. 2020/0229940, published Jul. 23, 2020, and entitled "Implant with Structural Members Arranged Around a Ring," which is a continuation of Bishop et al., U.S. Patent Application Publ. No. 2018/0256351, published Sep. 13, 2018, and entitled "Implant with Structural Members Arranged Around a Ring." The entire disclosures of the applications listed above are incorporated herein by reference.

BACKGROUND

The embodiments are generally directed to implants for supporting bone growth in a patient.

A variety of different implants are used in the body. Implants used in the body to stabilize an area and promote bone ingrowth provide both stability (i.e. minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection or tumor. The aim of the spinal fusion procedure is to reduce instability and thus pain.

In preparation for the spinal fusion, most of the intervertebral disc is removed. An implant, the spinal fusion cage, may be placed between the vertebra to maintain spine alignment and disc height. The fusion, i.e. bone bridge, occurs between the endplates of the vertebrae.

SUMMARY

In one aspect, an implant includes a body including a ring with an opening. The body defines a transverse plane dividing the implant into a superior half and an inferior half. The ring defines a radial direction and a circumferential direction. The implant includes a bone contacting member attached to the ring, where the bone contacting member extends radially from the ring. The implant also includes a support member attached to the bone contacting member at an attachment region, where the support member extends in the circumferential direction.

In another aspect, an implant includes a body. The body defines a transverse plane dividing the implant into a superior half and an inferior half. The implant includes a first bone contacting member attached to the body and disposed within the superior half of the implant. The implant also includes a first support member attached to the first bone contacting member, the first support member being disposed within the superior half of the implant. The implant also includes a second bone contacting member attached to the body and disposed within the inferior half of the implant. The implant also includes a second support member attached to the second bone contacting member, the second support member being disposed within the inferior half of the implant. An end of the first support member is attached to an end of the second support member.

In another aspect, an implant includes a body and a plurality of bone contacting members extending from a central region of the body to a periphery of the body. Each of the bone contacting members in the plurality of bone contacting members extend radially away from the central region of the body.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

DETAILED DESCRIPTION

The embodiments described herein are directed to an implant for use in a spine. The embodiments include implants with a body and one or more structural members. In addition to the various provisions discussed below, any embodiments may make use of any of the body/support structures, frames, plates, coils or other structures disclosed in Morris et al., U.S. Pat. No. 9,918,849, issued on Mar. 20, 2018, and titled "Coiled Implants and Systems and Methods of Use Thereof," which is hereby incorporated by reference in its entirety. For purposes of convenience, the Morris application will be referred to throughout the application as "The Coiled Implant Application". Also, any embodiments may make use of any of the body/support structures, elements, frames, plates or other structures disclosed in McShane III et al., U.S. Publication Number 2019/0000642, published on Jan. 3, 2019, and titled "Implant with Arched Bone Contacting Elements," which is hereby incorporated by reference in its entirety. Also, any embodiments may make use of any of the body/support structures, elements, frames, plates or other structures disclosed in McShane III et al., U.S. Publication Number 2018/0110626, published on Apr. 26, 2018, and titled "Implant with Protected Fusion Zones," which is hereby incorporated by reference in its entirety and referred to as "The Protective Fusion Zones application".

Figure 1:
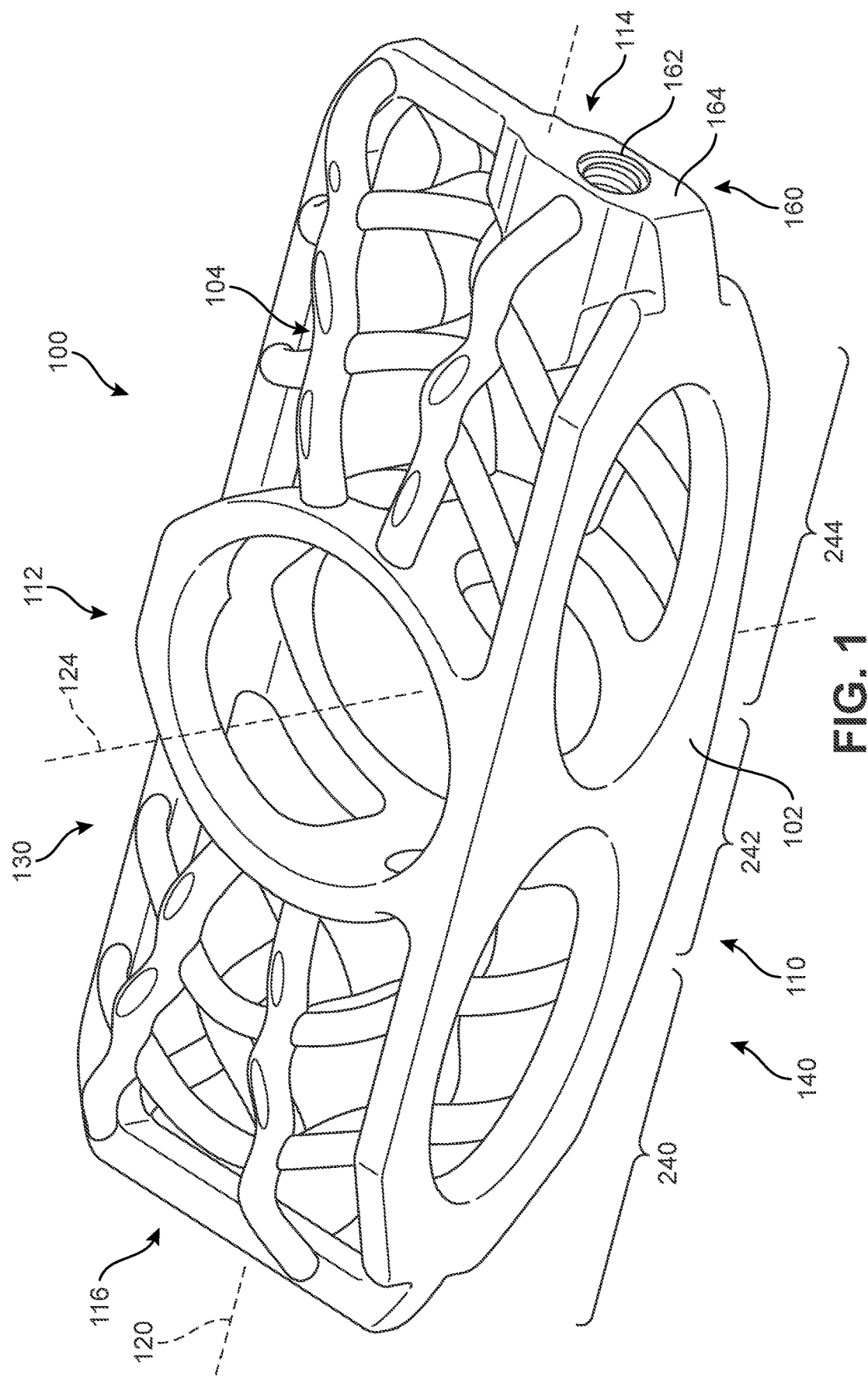
FIG. 1 is a schematic isometric superior view of an embodiment of an implant.
Figure 2:
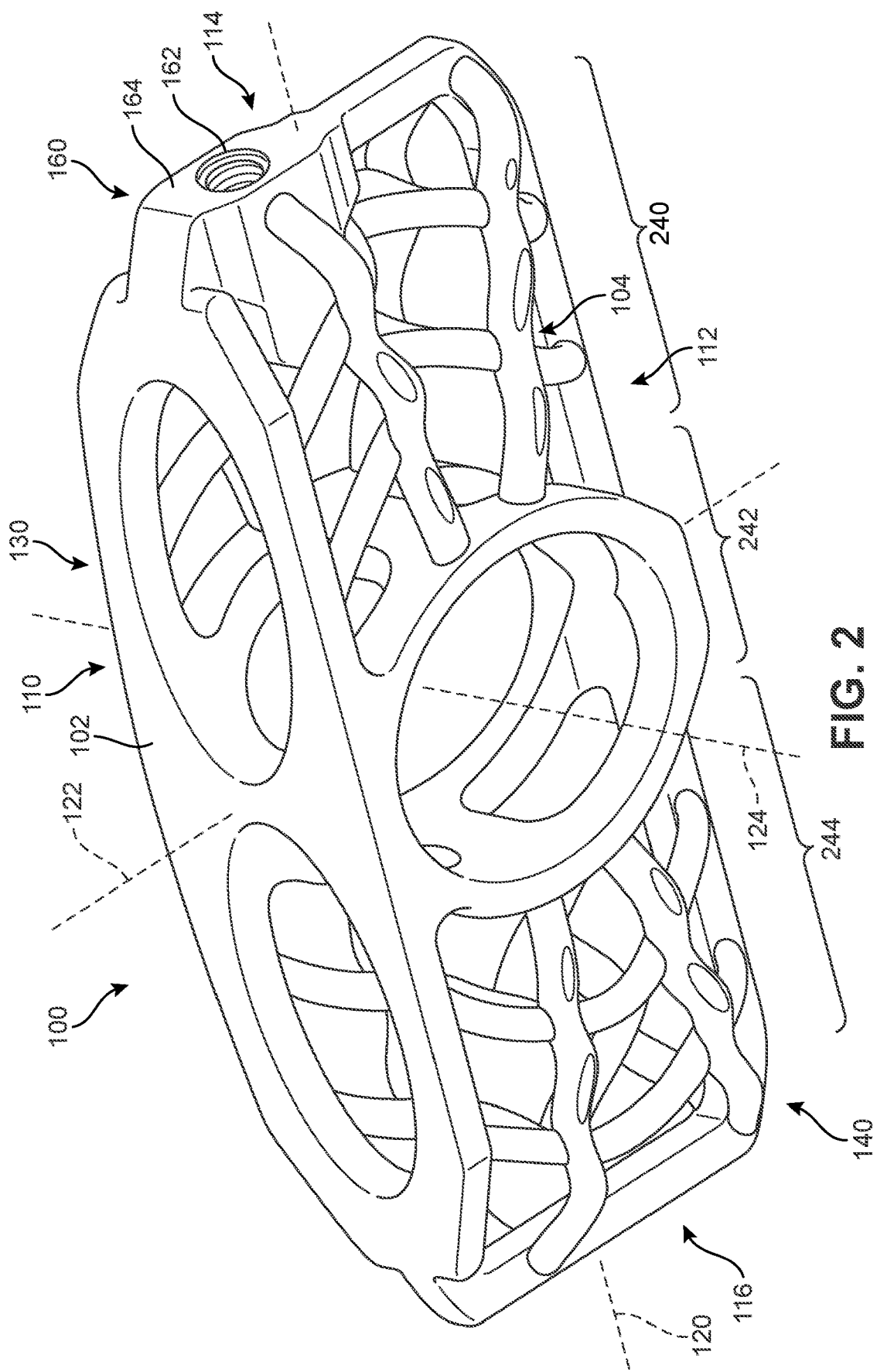
FIG. 2 is a schematic isometric inferior view of the implant of FIG. 1.

FIGS. 1 and 2 illustrate isometric views of an embodiment of an implant 100, which may be alternatively referred to as a device. Specifically, FIG. 1 is an isometric view of a top or superior side of implant 100, while FIG. 2 is an isometric view of a bottom or inferior side of implant 100. Implant 100 may also be referred to as a cage or fusion device. In some embodiments, implant 100 is configured to be implanted within a portion of the human body. In some embodiments, implant 100 may be configured for implantation into the spine. In some embodiments, implant 100 may be a spinal fusion implant, or spinal fusion device, that is inserted between adjacent vertebrae to provide support and/or facilitate fusion between the vertebrae.

In some embodiments, implant 100 may include a body 102. Body 102 may generally provide a frame or skeleton for implant 100. In some embodiments, implant 100 may also include a plurality of structural members 104. Plurality of structural members 104 may be fixedly attached to, and/or continuously formed (or "integrally formed") with, body 102. As used herein, the term "fixedly attached" shall refer to two components joined in a manner such that the components may not be readily separated (for example, without destroying one or both components).

As used herein, each structural member comprises a distinctive member or element that spans a portion of an implant. Structural members may overlap or intersect, similar to elements in a lattice or other 3D mesh structure. Some embodiments may use structural members in which the length of the member is greater than its width and its thickness. In embodiments where a structural member has an approximately circular cross-sectional shape, the structural member has a length greater than its diameter. In the embodiments seen in FIGS. 1-2, each structural member is seen to have an approximately rounded or circular cross-sectional shape (i.e., the member has the geometry of a solid tube). However, in other embodiments, a structural member could have any other cross-sectional shape, including, but not limited to, various polygonal cross-sectional shapes, as well as any other regular and/or irregular cross-sectional shapes. In some cases, for example, the cross-sectional size and/or shape of a structural member could vary along its length (e.g., the diameter could change along its length).

For purposes of clarity, reference is made to various directional adjectives throughout the detailed description and in the claims. As used herein, the term "anterior" refers to a side or portion of an implant that is intended to be oriented towards the front of the human body when the implant has been placed in the body. Likewise, the term "posterior" refers to a side or portion of an implant that is intended to be oriented towards the back of the human body following implantation. In addition, the term "superior" refers to a side or portion of an implant that is intended to be oriented towards a top (e.g., the head) of the body while "inferior" refers to a side or portion of an implant that is intended to be oriented towards a bottom of the body. Reference is also made herein to "lateral" sides or portions of an implant, which are sides, or portions, facing along a lateral direction of the body (which correspond with the left or right sides of a patient).

In FIGS. 1-2, implant 100 is understood to be configured with an anterior side 110 and a posterior side 112. Implant 100 may also include a first lateral side 114 and a second lateral side 116 that extend between the posterior side 112 and the anterior side 110 on opposing sides of implant 100. Furthermore, implant 100 may also include a superior side 130 and an inferior side 140.

Reference is also made to directions or axes that are relative to the implant itself, rather than to its intended orientation with regards to the body. For example, the term "distal" refers to a part that is located further from a center of an implant, while the term "proximal" refers to a part that is located closer to the center of the implant. As used herein, the "center of the implant" could be the center of mass and/or a central plane and/or another centrally located reference surface.

An implant may also be associated with various axes. Referring to FIG. 1, implant 100 may be associated with a longitudinal axis 120 that extends along the longest dimension of implant 100 between first lateral side 114 and second lateral side 116. Additionally, implant 100 may be associated with a posterior-anterior axis 122 (also referred to as a "widthwise axis") that extends along the widthwise dimension of implant 100, between posterior side 112 and anterior side 110. Moreover, implant 100 may be associated with a vertical axis 124 that extends along the thickness dimension of implant 100 and which is generally perpendicular to both longitudinal axis 120 and posterior-anterior axis 122.

An implant may also be associated with various reference planes or surfaces. As used herein, the term "median plane" refers to a vertical plane which passes from the anterior side to the posterior side of the implant, dividing the implant into right and left halves, or lateral halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric about two planes, such as the median and the transverse plane.

Figure 3:
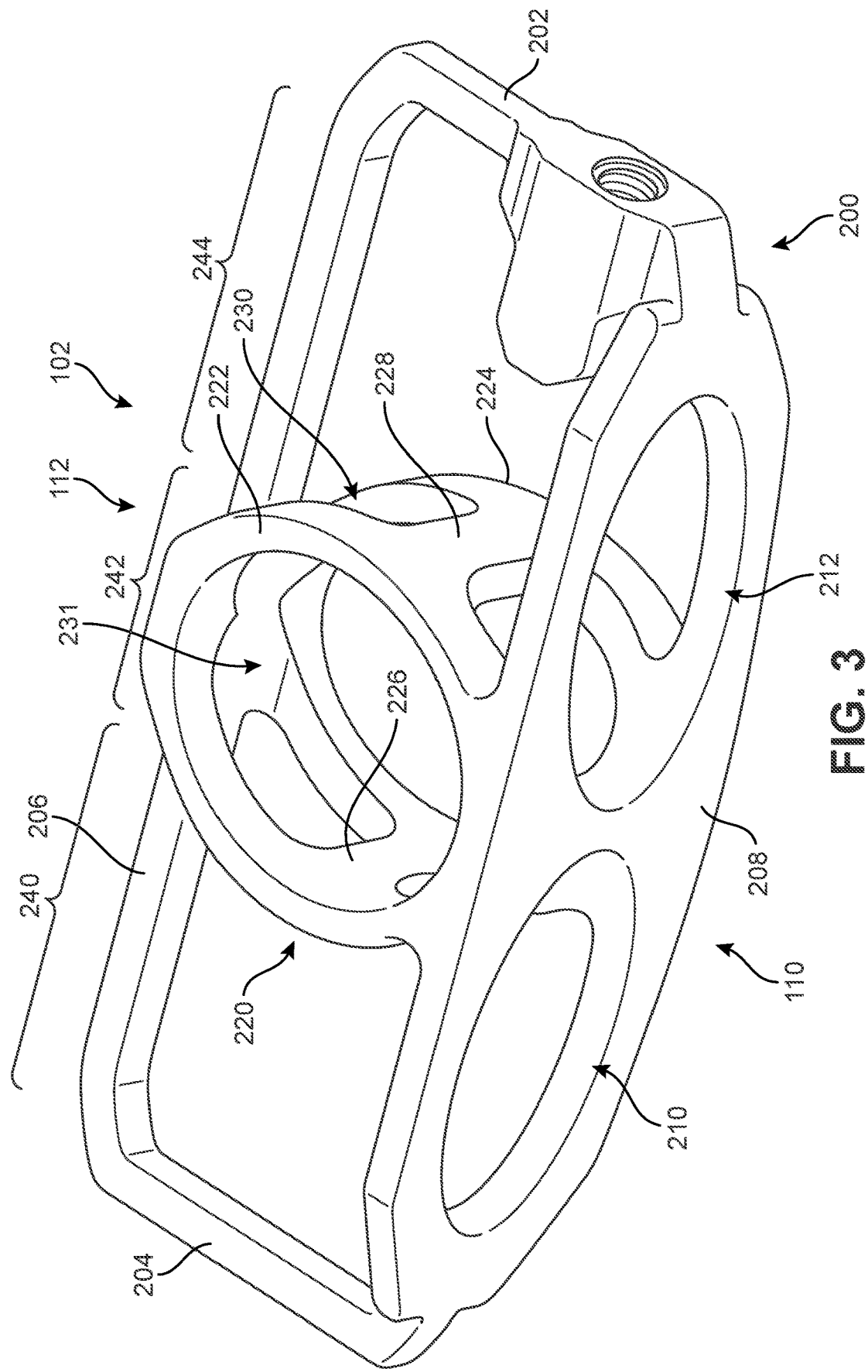
FIG. 3 is a schematic isometric view of a body of the implant of FIG. 1 shown in isolation.

FIG. 3 illustrates a schematic isometric view of body 102 in isolation, with plurality of structural members 104 removed for purposes of clarity. In some embodiments, a body could include distinct frame portions that are oriented in different directions. In the embodiment shown in FIG. 3, body 102 includes a peripheral frame portion 200, also referred to as simply "peripheral portion 200". In some embodiments, peripheral portion 200 has a longest dimension aligned with longitudinal axis 120 and a widthwise dimension (e.g., the second longest dimension) aligned with posterior-anterior axis 122 of implant 100 (see FIGS. 1 and 2). Peripheral frame portion 200 comprises a first lateral frame portion 202, a second lateral frame portion 204 and a posterior frame portion 206, which primarily lie in the transverse plane.

In some embodiments, one or more sides of an implant (including lateral sides and/or anterior/posterior sides) could include a vertically oriented peripheral frame portion. In the embodiment of FIG. 3, body 102 is seen to include a vertically oriented peripheral frame portion 208 disposed at anterior side 110, which may also be referred to as an "anterior wall" of implant 100. In contrast, posterior side 112 lacks any frame portion or wall that extends vertically beyond the thickness of peripheral portion 200 in the embodiments of FIGS. 3-4. The presence of vertically oriented peripheral frame portion 208 may improve support and strength against vertical loads applied along the anterior side of the spine.

Although the present embodiment uses a vertically oriented frame or wall on the anterior side of implant 100, in other embodiments, a vertically oriented frame or wall could be located on the posterior side of implant 100 and/or on a lateral side of implant 100. In still other embodiments, the implant may lack any vertical walls along its perimeter (i.e., along the posterior, anterior or lateral sides).

Embodiments may include one or more rings. In some embodiments, an implant could include two or more rings that are connected in a ring assembly. As seen in FIG. 3, body 102 includes a ring assembly 220. Ring assembly 220 is further comprised of a superior ring 222 and an inferior ring 224. Additionally, ring assembly 220 includes a first support 226 and a second support 228 which extend through an interior region (and intersect the transverse plane) of implant 100 and join superior ring 222 and inferior ring 224.

As seen in FIG. 3, ring assembly 220 may be arranged to form a hollow cylinder, which includes openings 230. This geometry may provide a tubular space (central cavity 231) through which bone growth from opposing vertebrae can extend through and fuse at the center of the implant, thereby forming a strong cylindrical column of bone growth. Furthermore, the presence of openings 230 may allow new bone growth to extend from the column and fuse with bone growth occurring in adjacent regions of the interior of implant 100. Optionally, in other embodiments, a ring assembly may comprise continuous cylindrical walls with no openings.

In different embodiments, the location of a ring assembly could vary. For purposes of characterizing possible locations of a ring assembly, an implant may be divided into a first lateral side region, a second lateral side region and a central region disposed between the first lateral side region and the second lateral side region. In the exemplary embodiment of FIG. 3, implant 100 includes a first lateral side region 240, a central region 242 and a second lateral side region 244. In the exemplary embodiment, therefore, ring assembly 220 is disposed in central region 242 and approximately equally spaced away from opposing lateral ends. Of course, in other embodiments, ring assembly 220 could be disposed in first lateral side region 240 or second lateral side region 244.

It may be appreciated that in other embodiments a ring assembly could be disposed centrally with respect to a posterior/anterior direction. Though, in the present embodiment, ring assembly 220 extends the full distance between the posterior and anterior edges of implant 100.

In different embodiments, the shape of a ring could vary. In the exemplary embodiment, superior ring 222 and inferior ring 224 each have an oval-like shape. However, in other embodiments, a ring could have any other shape including, but not limited to, a rounded shape, a circular shape, a triangular shape, a square shape, a polygonal shape, a regular shape, an irregular shape, etc.

A ring assembly, including a superior ring and an inferior ring, could be attached to other portions of the implant in various ways. In some embodiments, a ring assembly may be attached directly to a peripheral frame portion of a body. In other embodiments, a ring assembly could be attached to the body by way of one or more structural members. In the exemplary embodiment, ring assembly 220 is attached directly to both peripheral frame portion 206 and vertically oriented peripheral frame portion 208, while also being attached to a plurality of structural members (see FIGS. 1-2).

Figure 4:
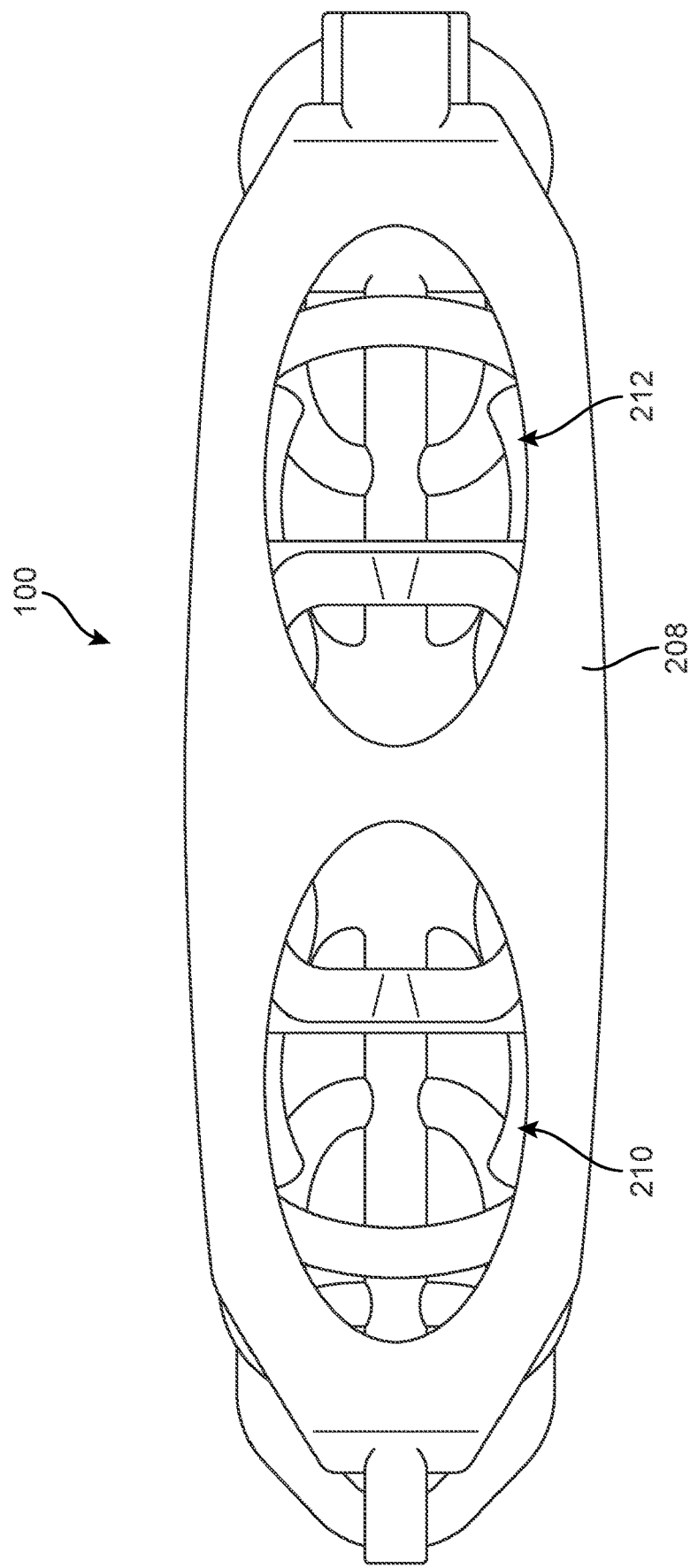
FIG. 4 is a schematic side view of the implant of FIG. 1.

FIG. 4 is a side view of an embodiment of implant 100. In some embodiments, vertically oriented peripheral frame portion 208 could include openings. In other embodiments, vertically oriented peripheral frame portion 208 may not include openings. In some embodiments, openings in a frame portion could provide an access point for inserting bone graft material or BGPM into an interior of an implant. The number, size and/or shape of openings in vertically oriented peripheral frame portion 208 could vary. In some cases, three or more openings could be used. In other cases, two openings could be used. In still other cases, a single opening could be used. Exemplary shapes for openings that could be used include, but are not limited to, rounded openings, rectangular openings, polygonal openings, regular openings and/or irregular openings. In the embodiment of FIGS. 3-4, vertically oriented peripheral frame portion 208 includes two large oval-shaped windows that may facilitate insertion of bone graft material (or BGMP) into an interior of the implant. Specifically, vertically oriented peripheral frame portion 208 includes first window 210 and second window 212.

Some embodiments can include provisions that facilitate implantation, including insertion and/or fixation of the implant. Some embodiments can include a fastener receiving portion. For example, as best seen in FIGS. 1-2, implant 100 includes a fastener receiving portion 160. Fastener receiving portion 160 includes a threaded opening 162 and a reinforced collar 164 to support threaded opening 162. In some embodiments, threaded opening 162 may be configured to receive a tool with a corresponding threaded tip to facilitate implantation of implant 100. In some embodiments, threaded opening 162 may be used with a screw to help attach implant 100 to a bone or another fixation device. In other embodiments, any other features for receiving fasteners and/or implantation tools could be incorporated into implant 100.

In some embodiments, an implant can be configured with one or more symmetries. In some cases, an implant may have a mirrored symmetry about one or more reference planes.

Referring to FIGS. 1 and 2, implant 100 may include at least one mirror symmetry. For purposes of reference, implant 100 may be split into a superior half and an inferior half. Here, the "superior half" of implant 100 includes the portions of body 102 and plurality of structural members 104 disposed above the transverse plane. Likewise, the "inferior half" of implant 100 includes the portions of body 102 and plurality of structural members 104 disposed below the transverse.

With respect to the transverse plane (which coincides generally with the plane defined by first lateral frame portion 202, second lateral frame portion 204 and posterior frame portion 206), it may be seen that the superior half of implant 100 mirrors the inferior half of implant 100, at least approximately. This includes not only the geometry of the body but also the shape, size and orientations of each structural member.

Moreover, with respect to the median plane (which approximately divides implant 100 into two lateral halves), it may be seen that two lateral halves mirror one another approximately. This includes not only the geometry of the body but also the shape, size and orientations of each structural member.

An implant may include two or more kinds of structural members (or structural elements). In some embodiments, an implant can include one or more bone contacting structural members, or simply "bone contacting members". Bone contacting members may generally be fully exposed on the outer surfaces of an implant, including along the superior and inferior sides of the implant. Thus, bone contacting members may be alternatively referred to as "outer members".

In some embodiments, an implant can include one or more structural members that provide support to one or more bone contacting members. Such supporting structural members may be referred to as "support members". In some embodiments, at least some portions of each support member may be hidden or covered by a bone contacting member or another element of the implant. Thus, support members may also be characterized as "inner members" as they are generally disposed inwardly of the bone contacting members.

Figure 5:
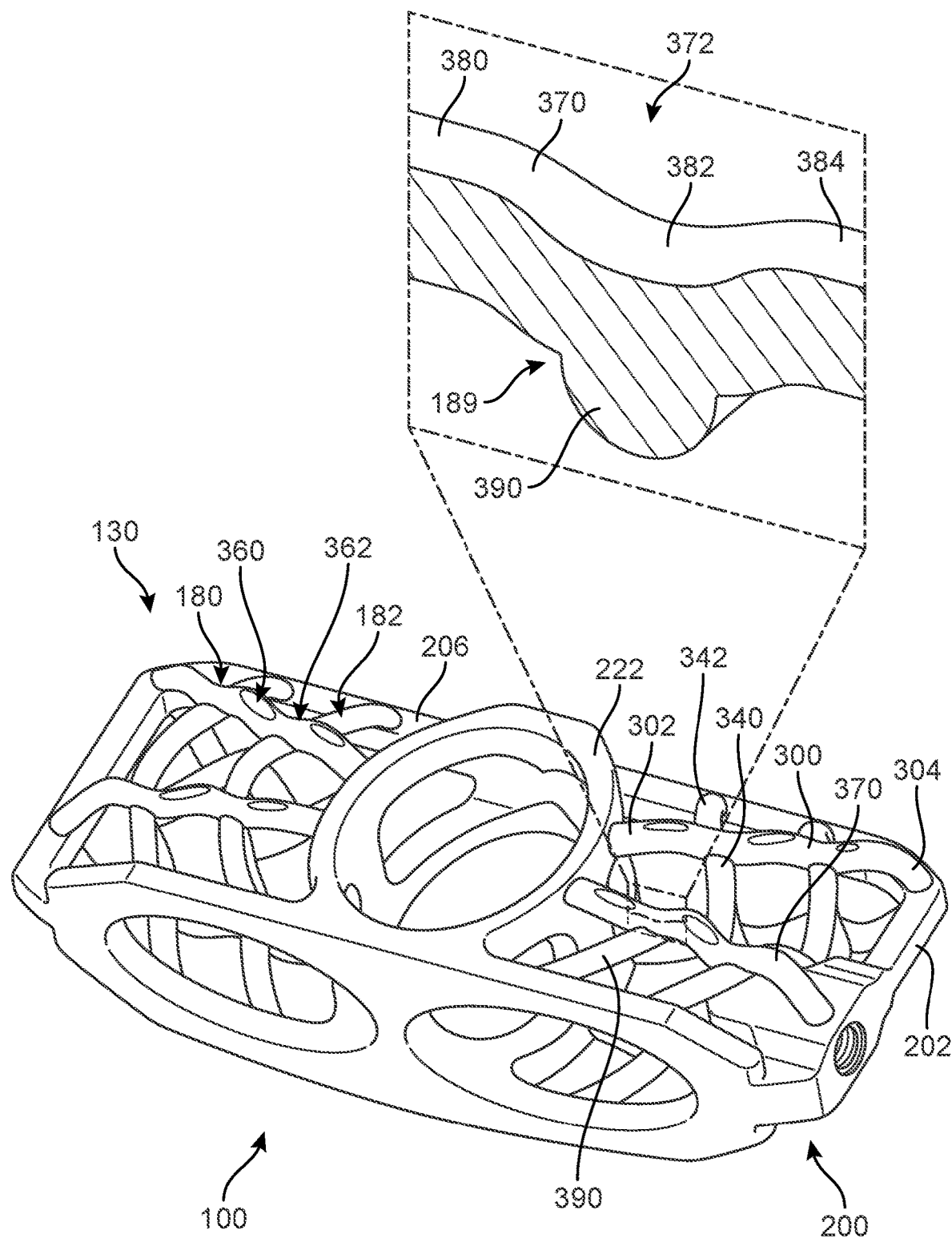
FIG. 5 is a schematic isometric view of the implant of FIG. 1, including an enlarged cut-away view of a structural member.

FIG. 5 illustrates a schematic isometric view of implant 100, according to an embodiment. As seen in FIG. 5, implant 100 may include a plurality of bone contacting members 180 as well as a plurality of support members 182. As best shown in FIGS. 1-2, plurality of structural members 104 are arranged in four distinct quadrants on implant 100: a first quadrant associated with superior side 130 and first lateral side region 240; a second quadrant associated with superior side 130 and a second lateral side region 244; a third quadrant associated with inferior side 140 and first lateral side region 240; and a fourth quadrant associated with inferior side 140 and second lateral side region 244.

The following discussion discusses exemplary structural members in some, but not all, of the quadrants of implant 100. However, it may be appreciated that similar properties and principles of the specific structural members discussed here may apply to structural members in any of the remaining quadrants.

In some embodiments, one or more structural members could be closed loops without ends. In other embodiments, at least some structural member comprises two ends. In some cases, structural members with two ends could include one or more ends that are attached to another structural member. In other cases, structural members with two ends could be arranged so that both ends are attached to a portion of a body of an implant. In the exemplary embodiment depicted in FIG. 5, each structural member includes two ends, with each end being attached to some portion of body 102, or attached to another structural member, of implant 100.

In some embodiments, an implant may include at least one bone contacting member with one end attached to a frame portion and another end attached to a central ring. For example, as seen in FIG. 5, a bone contacting member 300 includes a first end 302 attached to superior ring 222 and a second end 304 attached to first lateral frame 202.

In different embodiments, support members could be attached to different portions of an implant. In some embodiments, one or more ends of a support member could be attached to a peripheral frame portion of a body. In other embodiments, one or more ends could be attached to another support member. In still other embodiments, one or more portions of a support member could be attached to a bone contacting member. In one embodiment, each support member may be attached to a peripheral frame portion of the body, at least one bone contacting member, and at least one other support member.

In the exemplary embodiment of FIG. 5, each support member includes one end that is attached to a peripheral frame portion. For example, support member 340 includes a first end 342 that is attached to posterior frame portion 206. Likewise, the remaining support members of plurality of support members 182 each have an end attached to either peripheral frame portion 206 or vertically oriented peripheral frame portion 208.

Embodiments may include provisions to minimize the number of bars or other supports needed. Some embodiments may include provisions that eliminate the need for any internal supports extending between peripheral frame portion 200 (shown in FIG. 5) and ring assembly 220, thereby increasing the interior volume available to receive new bone growth. In some embodiments, support members from opposing superior and inferior sides of an implant may attach directly to one another, thereby eliminating the need for additional longitudinally running structures to receive the support members.

Figure 6:
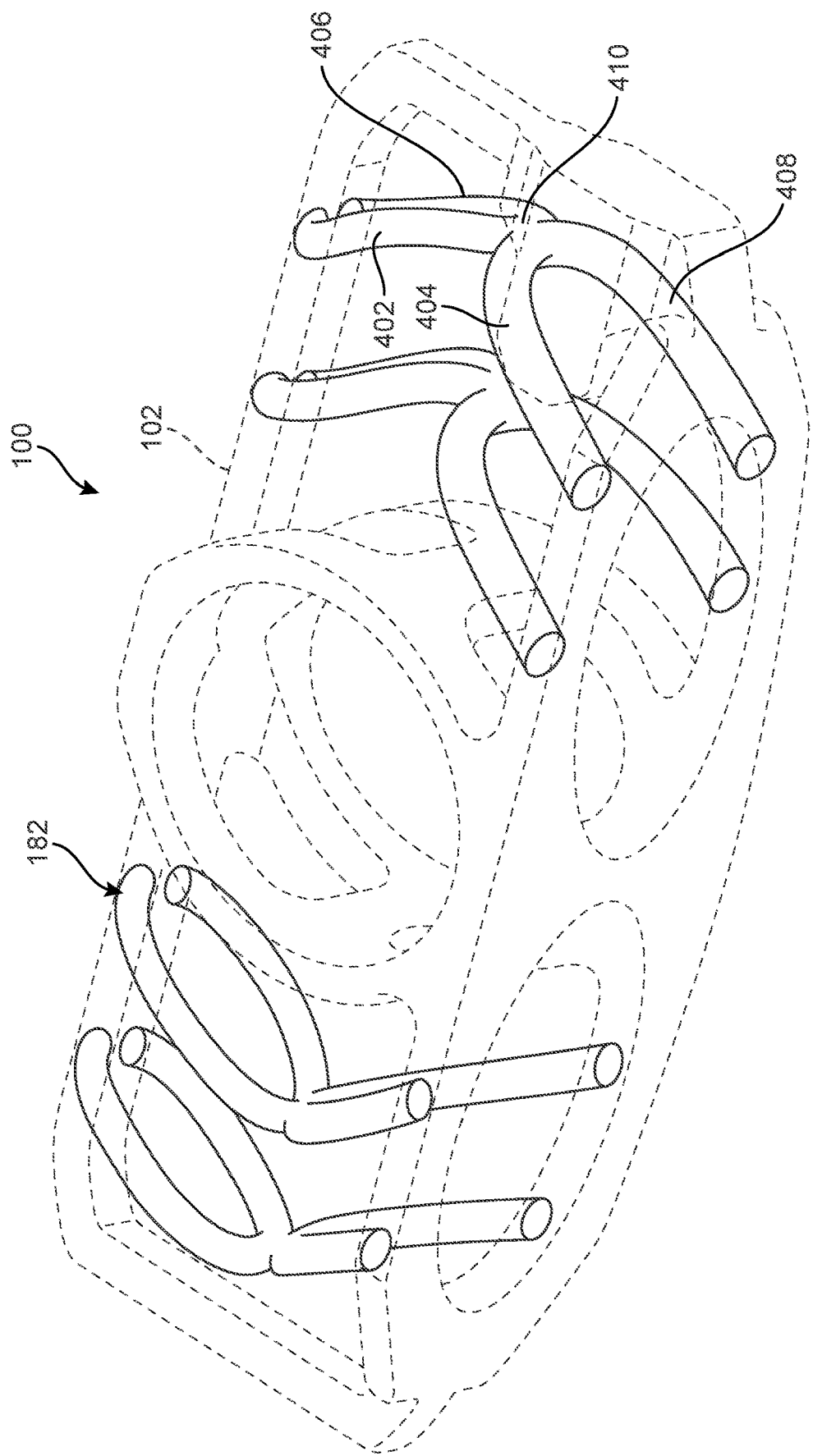
FIG. 6 is a schematic isometric view of a plurality of support members arranged within the body of the implant of FIG. 1.
Figure 7:
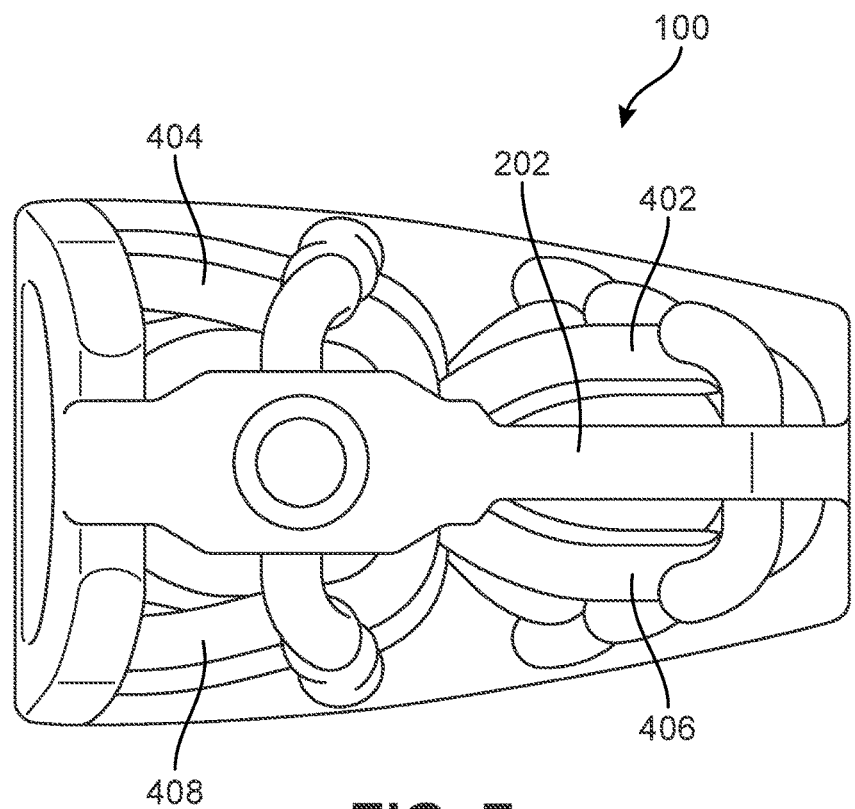
FIG. 7 is a schematic lateral side view of the implant of FIG. 1.
Figure 8:
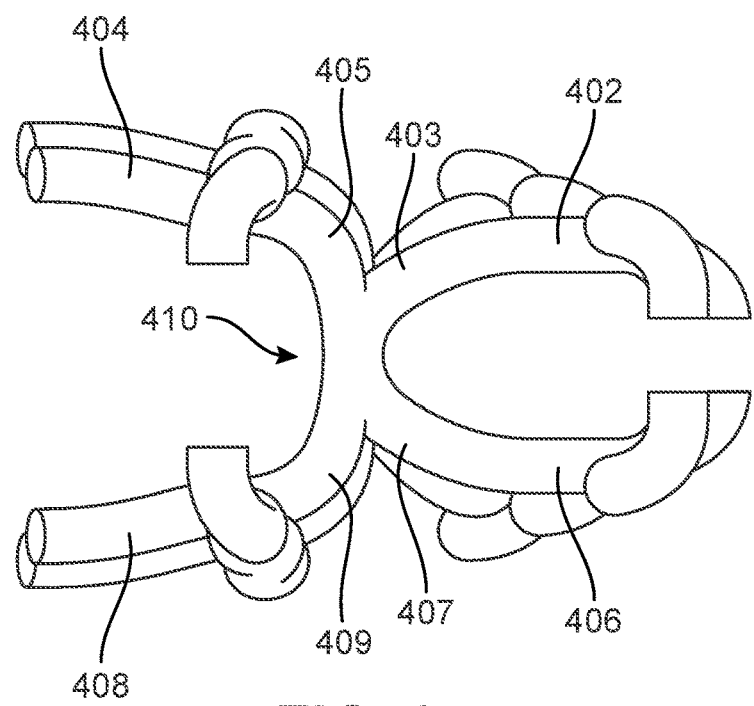
FIG. 8 is a schematic lateral side view of the implant of FIG. 1, in which the body has been removed for purposes of clarity.

FIG. 6 is a schematic isometric view of plurality of support members 182 with body 102 shown in phantom for purposes of clarity. FIG. 7 illustrates a schematic lateral end view of implant 100, while FIG. 8 illustrates a similar view with body 102 removed for purposes of illustration. As seen in FIGS. 6-8, each support member includes an end that is joined to three other support members at an area adjacent the transverse plane. As an example, first superior support member 402, second superior support member 404, first inferior support member 406 and second inferior support member 408 are all joined at an attachment region 410 that is located approximately in the transverse plane of implant 100. Specifically, as best seen in FIG. 8, an end 403 of first superior support member 402, an end 405 of second superior support member 404, an end 407 of first inferior support member 406 and an end 409 of second inferior support member 408 are all joined together. Using this arrangement, the support members provide reinforcement and support in both the posterior-anterior directions and vertical directions of implant 100 without requiring additional support elements (e.g., longitudinally running beams, bars or plates) that would serve as attachment points for the support members in the center of the implant.

In some embodiments, bone contacting members may be disposed distal to support members, with bone contacting members generally disposed further outwards along the superior and inferior sides of an implant. Thus, bone contacting members may generally be disposed closer to the vertebral end plates following implantation into the spine. Moreover, at regions where a bone contacting member is attached to a support member, the attached portion of the bone contacting member may be disposed distal to the attached portion of the inner member. As one example, FIG. 5 illustrates a schematic isometric view of implant 100 including an enlarged cross-sectional view of an attachment region 189 between bone contacting member 370 and support member 390. Here, bone contacting member 370 is seen to extend up and over support member 390. Moreover, bone contacting member 370 is seen to be located distally to support member 390. Here, distally is intended to mean disposed further from the transverse plane of implant 100.

Embodiments can include provisions for protecting bone growth along and adjacent to bone contacting members of an implant. In some embodiments, a bone contacting member can be configured with a geometry that helps to protect new bone growth in selected regions or "protected fusion zones". In some embodiments, a bone contacting member can have a spiral, helical or twisted geometry that provide a series of such protected fusion zones for enhanced bone growth.

Some bone contacting members may have a generalized helical geometry. As used herein, a "generalized helical geometry" or "spiraling geometry" refers to a geometry where a part (portion, member, etc.) winds, turns, twists, rotates or is otherwise curved around a fixed path. In some cases, the fixed path could be straight. In other cases, the fixed path can be curved. In the present embodiments, for example, the fixed path is generally a combination of straight segments and curved segments.

Curves having a generalized helical geometry (also referred to as generalized helical curves) may be characterized by "coils", "turns" or "windings" about a fixed path. Exemplary parameters that may characterize the specific geometry of a generalized helical curve can include coil diameter (including both a major and minor diameter) and the pitch (i.e., spacing between adjacent coils). In some cases, the "amplitude" of a coil or loop may also be used to describe the diameter or widthwise dimension of the coil or loop. Each of these parameters could be constant or could vary over the length of a generalized helical curve.

Generalized helical curves need not be circular or even round. In some embodiments, for example, a generalized helical curve could have linearly segmented shape (or locally polygonal shape) such that each "coil" or "turn" is comprised of straight line segments rather than arcs or other curved segments. Generalized helical curves may also include combinations of curved and straight segments. Examples of generalized helical curves are shown and described in The Protected Fusion Zones Application.

For purposes of characterizing the geometry of one or more structural members, each structural member can be understood to have a "central member curve". The central member curve of each structural member may be defined as a curve that extends along the length of the structural member such that each point along the curve is centrally positioned within the structural member.

In embodiments where a structural member winds or loops around a fixed path with an amplitude or diameter that is much greater than the cross-sectional diameter of the structural member itself, the structural member may be wound into visible distinct coils. Such coils are discussed in thorough detail in the Coiled Implant Application. In other embodiments, however, a structural member could be wound around a fixed path with an amplitude or diameter that is less than the cross-sectional diameter of the structural member itself. In such a case the resulting geometry of a structural member may appear to be twisted, but the geometry may lack the distinct coils seen in the Coiled Implant Application. However, it may be appreciated that while the outermost surface of such a structural member may not exhibit distinct coils, the central member curve of the structural member does have such coils or turns and moreover has a clear generalized helical geometry.

Figure 9:
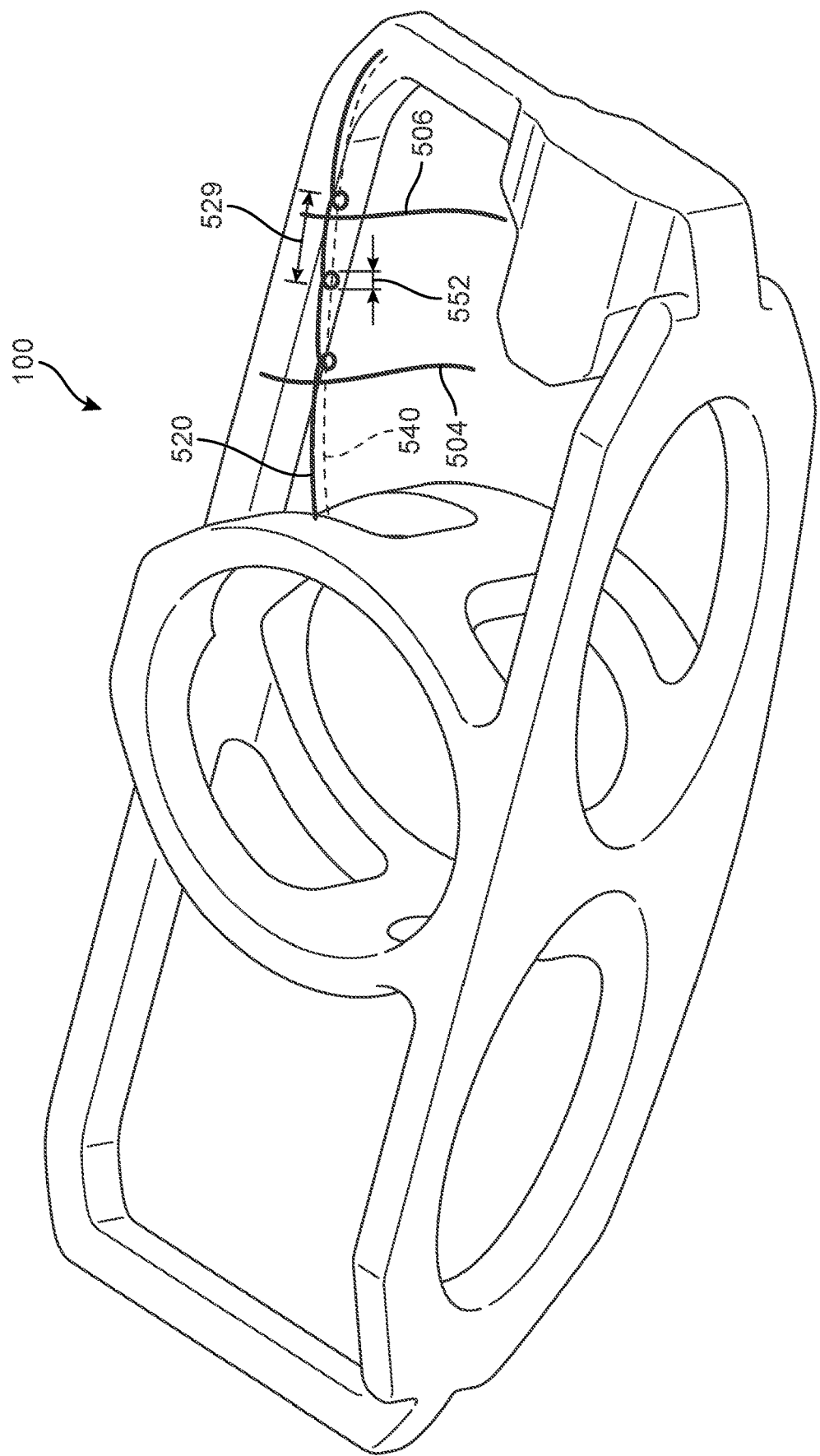
FIG. 9 is a schematic isometric view of the implant of FIG. 1, in which member curves of several structural members are illustrated.

FIG. 9 is a schematic isometric view of implant 100 where the structural members have been removed for purposes of clarity. To depict the geometry of the structural members, the central member curve of several structural members is shown. Specifically, central member curve 520 is shown, which corresponds to the geometry of bone contacting member 300. Additionally, central member curve 504 and central member curve 506 are shown, which correspond with the geometry of support members providing support to bone contacting member 300.

As previously discussed, bone contacting member 300 (FIG. 5) exhibits a twisted geometry indicative of a spiral or helix. However, since the winding occurs with an amplitude much smaller than the thickness of bone contacting member 300, the geometry of the part may be difficult to discern. The generalized helical geometry of bone contacting member 300 becomes much clearer when the geometry of its central member curve 520 (which is clearly seen in FIG. 9) is considered as it winds around a fixed path 540 (also shown in FIG. 9).

In different embodiments, the winding diameter of a helical structural member could vary. In the exemplary embodiment, a winding diameter 552 of the coils or turns in central member curve 520 are smaller than the diameter of bone contacting member 300. In other embodiments, the cross-sectional diameter of a bone contacting member could be less than a corresponding winding diameter of the coils or turns of its central member curve. In such an embodiment, the bone contacting member would be configured in a series of distinct coils.

A bone contacting member may not have a generalized helical geometry through its entire length. Instead, its central member curve may be configured with a winding segment where the central member curve completes several full turns (three in FIG. 9) around a fixed path. Away from the winding segment, its central member curve may not include any turns, twists, etc.

Although the present embodiment includes at least one bone contacting member with a winding segment that makes one or more full turns around a fixed path, other embodiments could be configured with central member curves that only make partial turns around a fixed path.

While the description here has focused on the geometry of a single bone contacting member 300, it may be appreciated that some or all of the remaining bone contacting members in plurality of structural members 104 may have a similar generalized helical geometry. It may be further appreciated that two different bone contacting members could have slightly different geometries, with distinct bone contacting member curves that include variations in the number of windings, shape of the windings, etc.

In some embodiments, an implant can include bone contacting members that are locally helical over small distances compared to the length, width or height of the implant. For example, implant 100 may be characterized as having bone contacting members that are locally helical or locally spiraling, rather than globally helical. In particular, each bone contacting member of implant 100 is bounded within a single quadrant of implant 100 and does not cross the transverse plane or the median plane of implant 100. Thus, a full turn of the bone contacting members is accomplished over distances that are much smaller than half the length, width or height of the implant. This allows multiple windings within each quadrant of the implant and also results in the pitch between windings being smaller than the length, width or height of the implant. For example, in FIG. 9, central member curve 520 has a pitch 529 between adjacent windings or turns that is less than one third of the length of bone contacting member 300. Pitch 529 is also less than one tenth of the length of implant 100. This relatively small pitch size allows for a greater number of proximal surface regions along each bone contacting member, thereby increasing the number of available protected fusion zones of the inferior and superior surfaces of implant 100.

In some embodiments, the helix-like geometry of bone contacting members provides distinct regions exposed on the superior and inferior sides of an implant. For example, referring to FIG. 5, each bone contacting member includes one or more distal regions 360 that may be seen as "peaks" in the bone contacting member along the superior side 130 of implant 100. In at least some embodiments, these distal regions 360 may be flattened or "smoothed" to provide a flat or smooth distal-most surface on superior side 130 (and inferior side 140), thereby facilitating contact with adjacent vertebrae. In other embodiments, a distal surface region may be curved. In some cases, the distal surface region could have a curvature that matches the curvature of the adjacent surface regions of the bone contacting member. In other cases, the distal surface region could have a different curvature (e.g., more convex) than adjacent surface regions of the bone contacting member.

Bone contacting members may also include proximal regions 362 that are configured as "valleys" in the bone contacting member along the superior side 130 of implant 100. Whereas the distal regions 360 may come into contact with the vertebrae during and following implantation of implant 100, proximal regions 362 may be recessed or spaced apart from direct contact with the vertebrae, at least before new bone growth has developed.

As a particular example, FIG. 5 includes an enlarged cross-sectional view of a portion of a bone contacting member 370 and underlying support member 390. Specifically, an outwardly facing surface portion 372 of bone contacting member 370 is visible. As used herein, the "outwardly facing surface portion" of a bone contacting member is the portion of the surface of the bone contacting member facing towards a vertebra during implantation, or facing away from an interior of the implant. Outwardly facing surface portion 372 includes a first distal surface region 380, a proximal surface region 382 and a second distal surface region 384. As discussed in further detail below, this local geometry provides a series of protected fusion zones adjacent each proximal surface region, where new bone growth can be protected during early bone fusion.

While bone contacting members may have generalized helical geometries, the geometries of the support members may be selected to enhance strength and support. In some embodiments, support members could have a generally tube-like (solid) shape and may extend in simple curves from one portion of a body to another. In some cases, the central member curve of a support member may be smoothly curved without any local twists, windings or coils.

Thus, it may be appreciated, that in some embodiments, support members may generally be shorter and their geometry may be more arch-like to improve strength and provide increased support for the bone contacting members. In contrast, the bone contacting members may generally have a longer length and may be less arch-like in shape relative to the support members, as the bone contacting members need to extend across as much of the superior/inferior sides of an implant as possible to provide contact with the vertebrae.

While some embodiments include bone contacting members with generalized helical geometries and support members with arch-like geometries, in other embodiments any structural member could be configured with any type of geometry. For example, in another embodiment, one or more support members could have a generalized helical geometry that create protected fusion zones along the support members. In still another embodiment, one or more bone contacting members could have an arch-like geometry.

In different embodiments, the attachment between a support member and a bone contacting member could occur at various locations. In some embodiments, a support member could be attached near a distal surface region along the outer surface of a bone contacting member. In other embodiments, a support member could be attached near a proximal surface region along the outer surface of a bone contacting member.

In some embodiments, each support member is configured to attach to a corresponding bone contacting member at a location adjacent (or underlying) a proximal surface region of the bone contacting member. For example, as shown in FIG. 5, an attachment region 189 of support member 390 is attached to bone contacting member 300 at a location corresponding to proximal surface region 382 of bone contacting member 300. Likewise, every other support member of implant 100 attaches to one or more bone contacting members only at locations corresponding to proximal surface regions.

This configuration provides for protected fusion zones that encompass the space immediately adjacent the proximal regions. The protected fusion zones are locations along the superior/inferior surfaces of an implant where new bone growth can be partially protected from forces applied to the bone contacting members by adjacent support members or directly from a vertebra.

By configuring one or more bone contacting members with at least one helical portion, the bone contacting member may provide one or more protected fusion zones on the superior and inferior sides of an implant. These protected fusion zones encompass the space immediately adjacent the proximal regions of the bone contacting members. The recessed spaces provided by the proximal regions allow for pockets of new bone growth adjacent initial fusion that may occur at the distal regions. Moreover, because the support members are attached near the proximal surface regions, and not at the distal surface regions, forces applied to the bone contacting members by either the support members or by a vertebra can be directed away from the protected fusion zones, thereby minimizing the disturbance of new bone growth.

Figure 10:
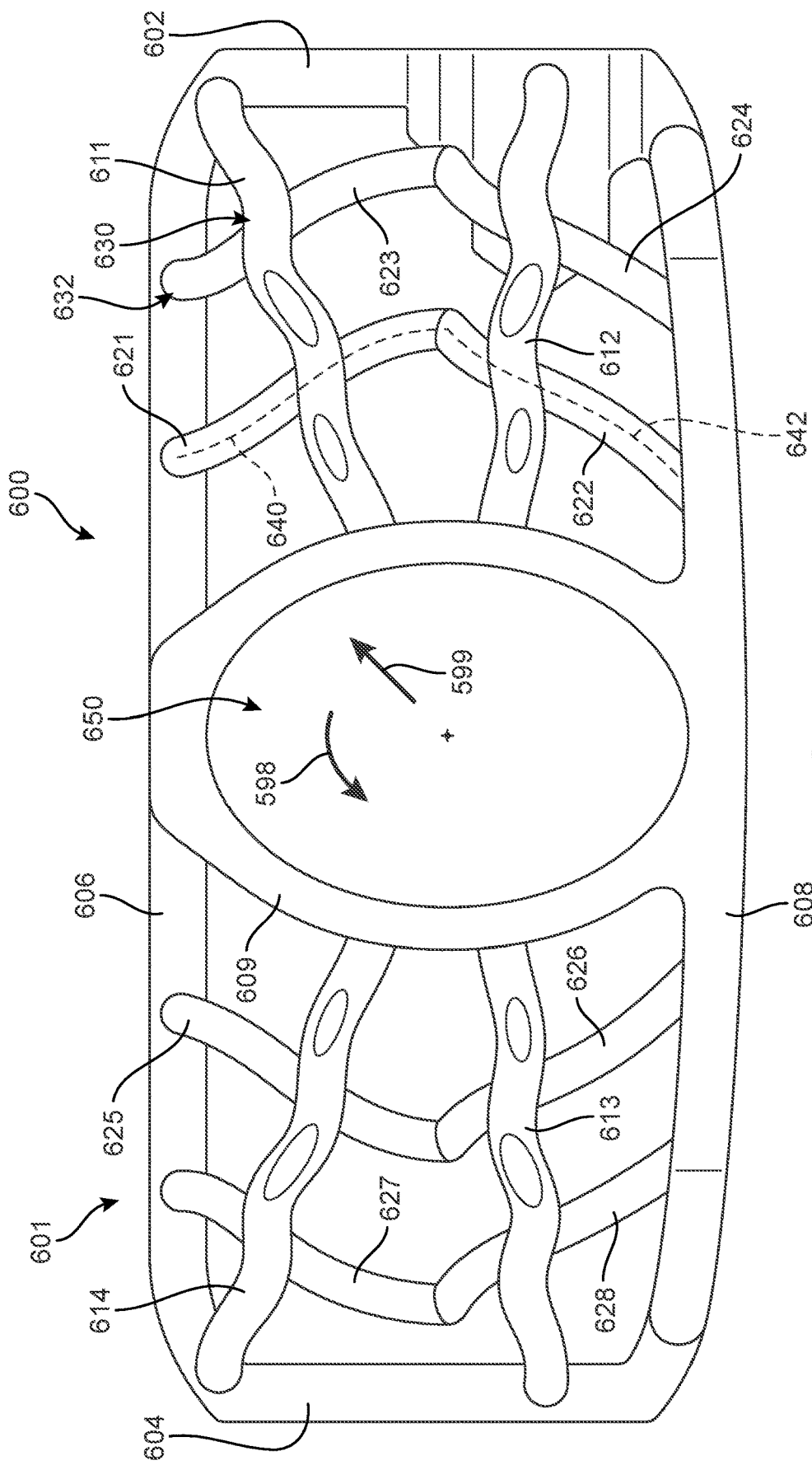
FIG. 10 is a schematic superior view of an embodiment of an implant.

FIG. 10 is a schematic top down view of an implant 600, according to an embodiment. Referring to FIG. 10, implant 600 includes body 601 comprising peripheral frame portion 602, peripheral frame portion 604, peripheral frame portion 606 and peripheral frame portion 608. Additionally, body 601 comprises ring 609 defining a central opening 650.

For purposes of reference, central opening 650 (and ring 609) define a radial direction 599 and a circumferential direction 598. Here, radial direction 599 extends outwardly from a center of central opening 650, while circumferential direction 598 is an angular direction that is perpendicular with radial direction 599.

In different embodiments, the orientation of bone contacting members and/or support members could vary. In some embodiments, bone contacting members may be oriented radially away from a center of an implant. In some embodiments, support members may be oriented in a circumferential (or angular) direction that rotates about a center of an implant. In other embodiments, however, bone contacting members could be oriented in a circumferential direction while support members could be oriented in a radial direction. In still other embodiments, one or more structural elements could be oriented in directions orthogonal to the length and/or width of an implant, rather than in radial and/or circumferential directions.

Implant 600 also includes plurality of bone contacting members 630 and plurality of support members 632. As seen in FIG. 10, plurality of bone contacting members 630, which includes first bone contacting member 611, second bone contacting member 612, third bone contacting member 613 and fourth bone contacting member 614 may each extend in radial direction 599 (i.e., outwardly from central opening 650 and ring 609). For example, first bone contacting member 611 extends radially from ring 609 to peripheral frame portion 602. Second bone contacting member 612 also extends radially from ring 609 to peripheral frame portion 602, though second bone contacting element 612 has a different angular (or circumferential) position along circumferential direction 598. Also, third bone contacting member 613 extends radially from ring 609 to peripheral frame portion 604. Fourth bone contacting member 614 also extends radially from ring 609 to peripheral frame portion 604, though fourth bone contacting element 614 has a different angular (or circumferential) position along circumferential direction 598.

As seen in FIG. 10, plurality of support members 632 is further comprised of first support member 621, second support member 622, third support member 623, fourth support member 624, fifth support member 625, sixth support member 626, seventh support member 627 and eighth support member 628. Each of these support members may be oriented approximately in the circumferential direction 598. For example, first support member 621 extends from peripheral frame portion 606 to its attachment with second support member 622 along a path 640 that is approximately parallel with the circumferential direction 598. Likewise, second support member 622 extends from its attachment to first support member 621 to peripheral frame portion 608 along a path 642 that is also approximately parallel with circumferential direction 598. Moreover, it is clear from FIG. 10 that first support member 621 is approximately perpendicular with (radially oriented) first bone contacting member 611 and that second support member 622 is approximately perpendicular with (radially oriented) second bone contacting member 612. Similarly, each remaining support member in plurality of support members 632 is oriented approximately parallel with circumferential direction 598 and is also approximately perpendicular to a bone contacting member to which it attaches.

The embodiment of FIG. 10 may be characterized as having structural members arranged in a web-like or spider web-like pattern. Moreover, it may be appreciated that while only one side of implant 600 is shown, an opposing side may likewise include a central ring and structural members oriented in a similar web-like pattern.

This web-like pattern provides radially oriented structural members (bone contacting members) that may help improve strength in multiple directions simultaneously (i.e., the longitudinal and lateral directions). This may also help direct new bone growth from the center of the device (which includes a large central cavity for bone growth) towards the corners and periphery of the device. Moreover, the circumferential orientation of some structural members (support members) in this web-like pattern also improves the strength of the device in multiple directions simultaneously and in directions orthogonal to the radially oriented structural members.

The arrangement of structural members with the body may also be designed to achieve a desired total open volume. As used herein a total volume is the combined volume of any openings between structural members, any openings in the body, or between structural members and the body. This open configuration may facilitate bone growth in and through the implant. A portion, or substantially all of, the open spaces is optionally filled with a bone graft or bone growth promoting material prior to or after insertion of the implant to facilitate bone growth.

The total volume of the open spaces (also referred to simply as the open space volume) within any particular implant is dependent on the overall dimension of the implant as well as the size and dimension of individual components within the implant including structural members, frame portions, etc. The open space volume may range from about 20% to 80% of the volume of the implant. In some embodiments, implant 100 may have an open space volume that is between 25% and 80% of the implant's total volume. In still further embodiments, implant 100 may have an open space volume that is between 40% and 75% of the total implant volume.

Figure 11:
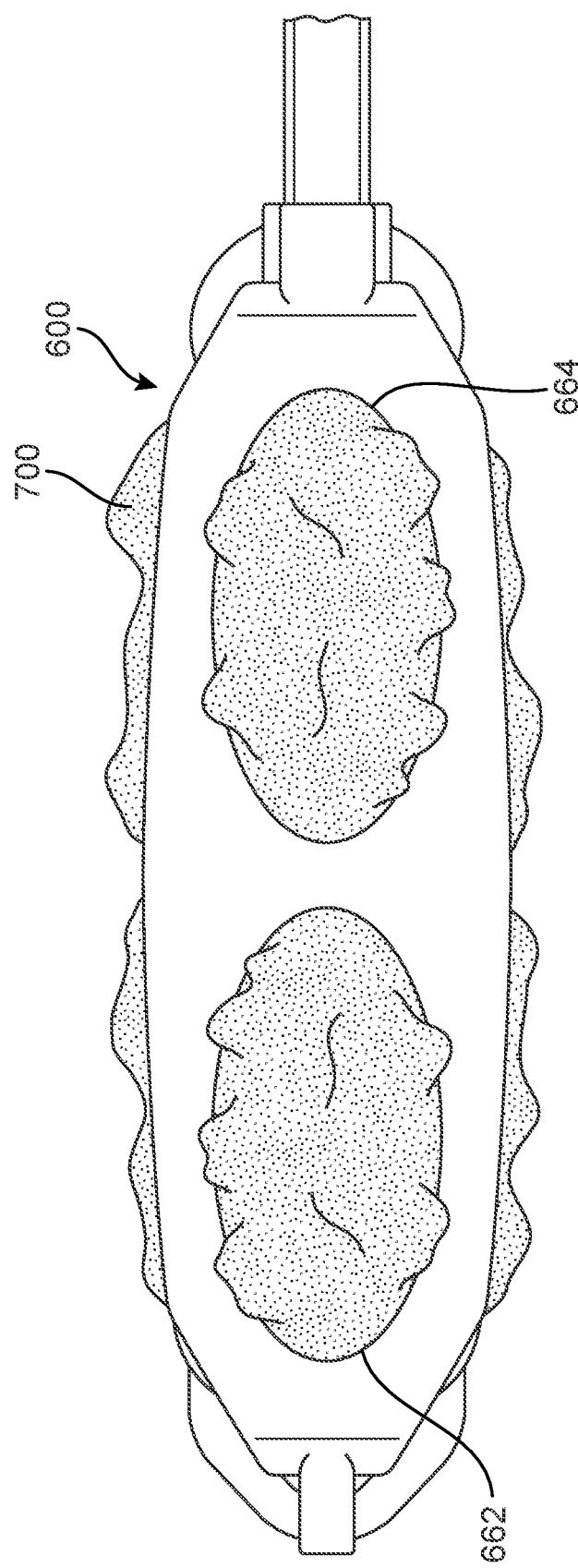
FIG. 11 is a schematic depicting an implant attached to an implant tool, and where the implant is covered with a bone growth promoting material, according to an embodiment.
Figure 12:
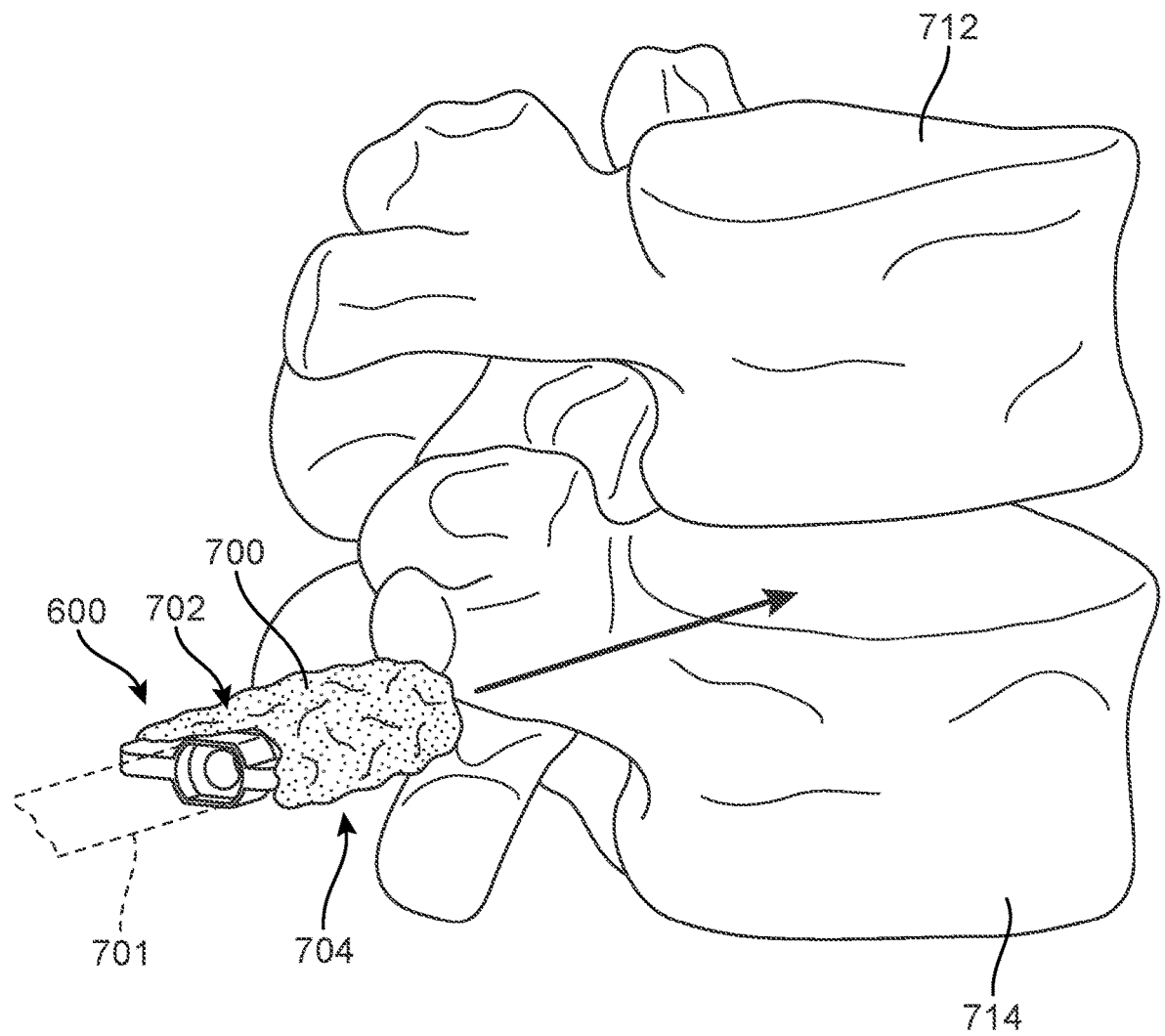
FIG. 12 is a schematic isometric view of an implant being positioned for insertion between two vertebrae, according to an embodiment.
Figure 13:
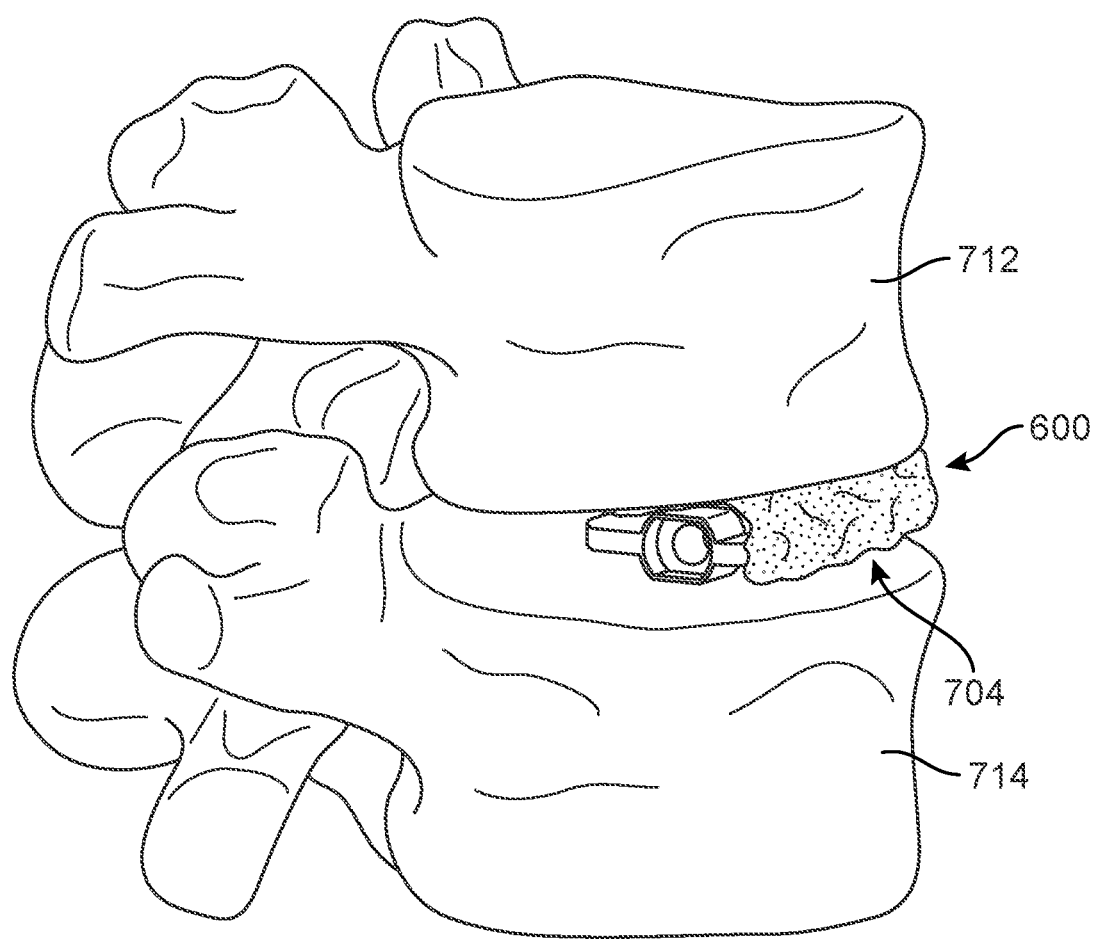
FIG. 13 is a schematic isometric view of the implant of FIG. 12 inserted between the two vertebrae.

FIGS. 11-13 illustrate various schematic views of a process of implanting an implant 600. Referring first to FIGS. 11-13, the implantation process may begin with the application of a bone growth promoting material, also referred to as a BGPM, to the implant. As used herein, a "bone growth promoting material" is any material that helps bone growth. Bone growth promoting materials may include provisions that are freeze dried onto a surface or adhered to the metal through the use of linker molecules or a binder. Examples of bone growth promoting materials are any materials including bone morphogenetic proteins (BMPs), such as BMP-1, BMP-2, BMP-4, BMP-6, and BMP-7. These are hormones that convert stem cells into bone forming cells. Further examples include recombinant human BMPs (rhBMPs), such as rhBMP-2, rhBMP-4, and rhBMP-7. Still further examples include platelet derived growth factor (PDGF), fibroblast growth factor (FGF), collagen, BMP mimetic peptides, as well as RGD peptides. Generally, combinations of these chemicals may also be used. These chemicals can be applied using a sponge, matrix or gel.

Some bone growth promoting materials may also be applied to an implantable prosthesis through the use of a plasma spray or electrochemical techniques. Examples of these materials include, but are not limited to, hydroxyapatite, beta tri-calcium phosphate, calcium sulfate, calcium carbonate, as well as other chemicals.

A bone growth promoting material can include, or may be used in combination with, a bone graft or a bone graft substitute. A variety of materials may serve as bone grafts or bone graft substitutes, including autografts (harvested from the iliac crest of the patient's body), allografts, demineralized bone matrix, and various synthetic materials.

Some embodiments may use autograft. Autograft provides the spinal fusion with calcium collagen scaffolding for the new bone to grow on (osteoconduction). Additionally, autograft contains bone-growing cells, mesenchymal stem cells and osteoblast that regenerate bone. Lastly, autograft contains bone-growing proteins, including bone morphogenic proteins (BMPs), to foster new bone growth in the patient.

Bone graft substitutes may comprise synthetic materials including calcium phosphates or hydroxyapatites, stem cell containing products which combine stem cells with one of the other classes of bone graft substitutes, and growth factor containing matrices such as INFUSE® (rhBMP-2-containing bone graft) from Medtronic, Inc.

It should be understood that the provisions listed here are not meant to be an exhaustive list of possible bone growth promoting materials, bone grafts or bone graft substitutes.

In some embodiments, BGPM may be applied to one or more outer surfaces of an implant. In other embodiments, BGPM may be applied to internal volumes within an implant. In still other embodiments, BGPM may be applied to both external surfaces and internally within an implant. As seen in FIGS. 11-13, a BGPM 700 has been placed inside an interior of implant 600 and also applied on superior and inferior surfaces of implant 600. Moreover, as shown in FIG. 11, BGPM 700 has been inserted through (and extends through) a first window 662 and a second window 664 of implant 600.

FIGS. 12 and 13 show schematic views of the implant pre-implantation (FIG. 12) and post-implantation (FIG. 13). Once implanted, implant 600 may be disposed between, and in direct contact with, adjacent vertebra. Specifically, a superior side 702 of implant 600 is disposed against first vertebra 712. Likewise, an inferior side 704 of implant 600 is disposed against second vertebra 714.

In different embodiments, implantation methods could vary. In some embodiments, implant 600 may be secured to an implantation tool 701 (partially seen in FIGS. 11-12) that is used to drive implant 600 into the spine. Implantation tool 701 could be any rod, ram, pole or other device that can be hammered, rammed, or otherwise driven to position implant 600 between adjacent vertebrae. As previously mentioned, in some cases, an implantation tool could be attached to implant 600 at a fastener receiving portion (i.e., a threaded opening for receiving a threaded shaft from a tool).

FIGS. 14-20 depict a schematic sequence of bone growth throughout implant 600, including through central cavity 671 (FIGS. 14-16), as well as along the superior and inferior sides of implant 600 (FIGS. 17-20).

Figure 14:
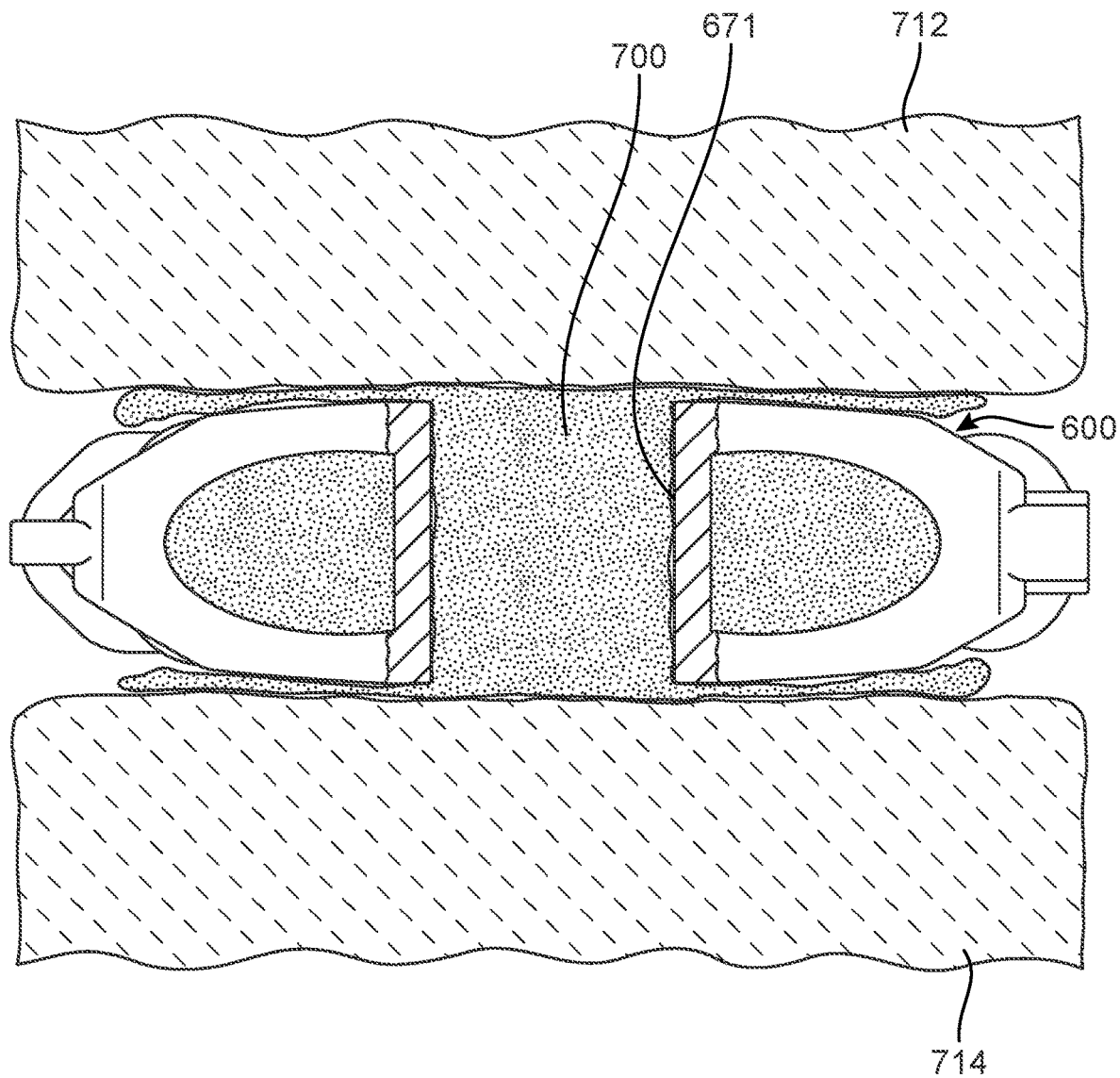
FIG. 14 is a schematic side view of the implant of FIG. 13 including a partial cut-away view of a central cavity.
Figure 15:
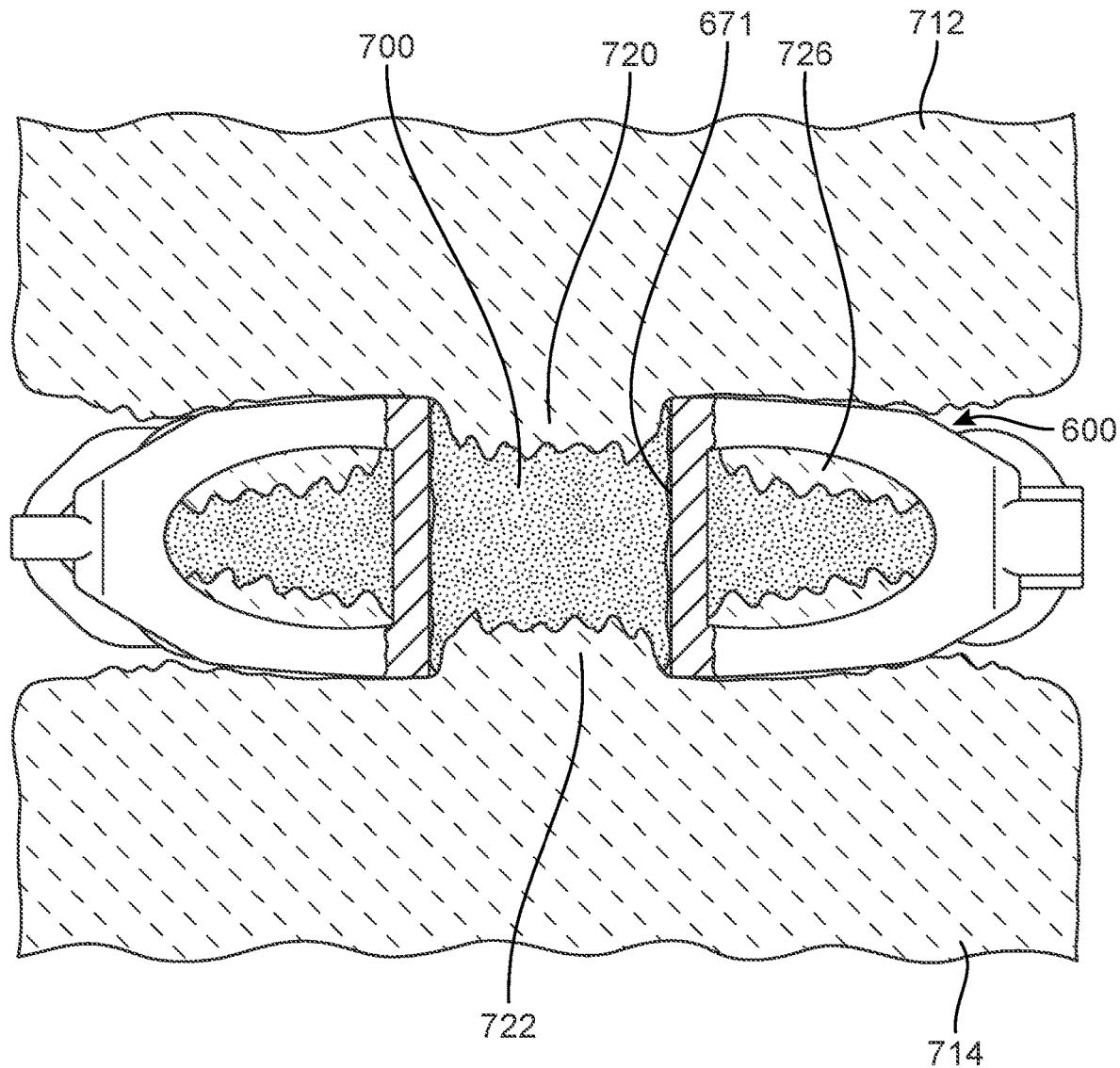
FIG. 15 is a schematic side view of the implant of FIG. 13 indicating areas of new bone growth.
Figure 16:
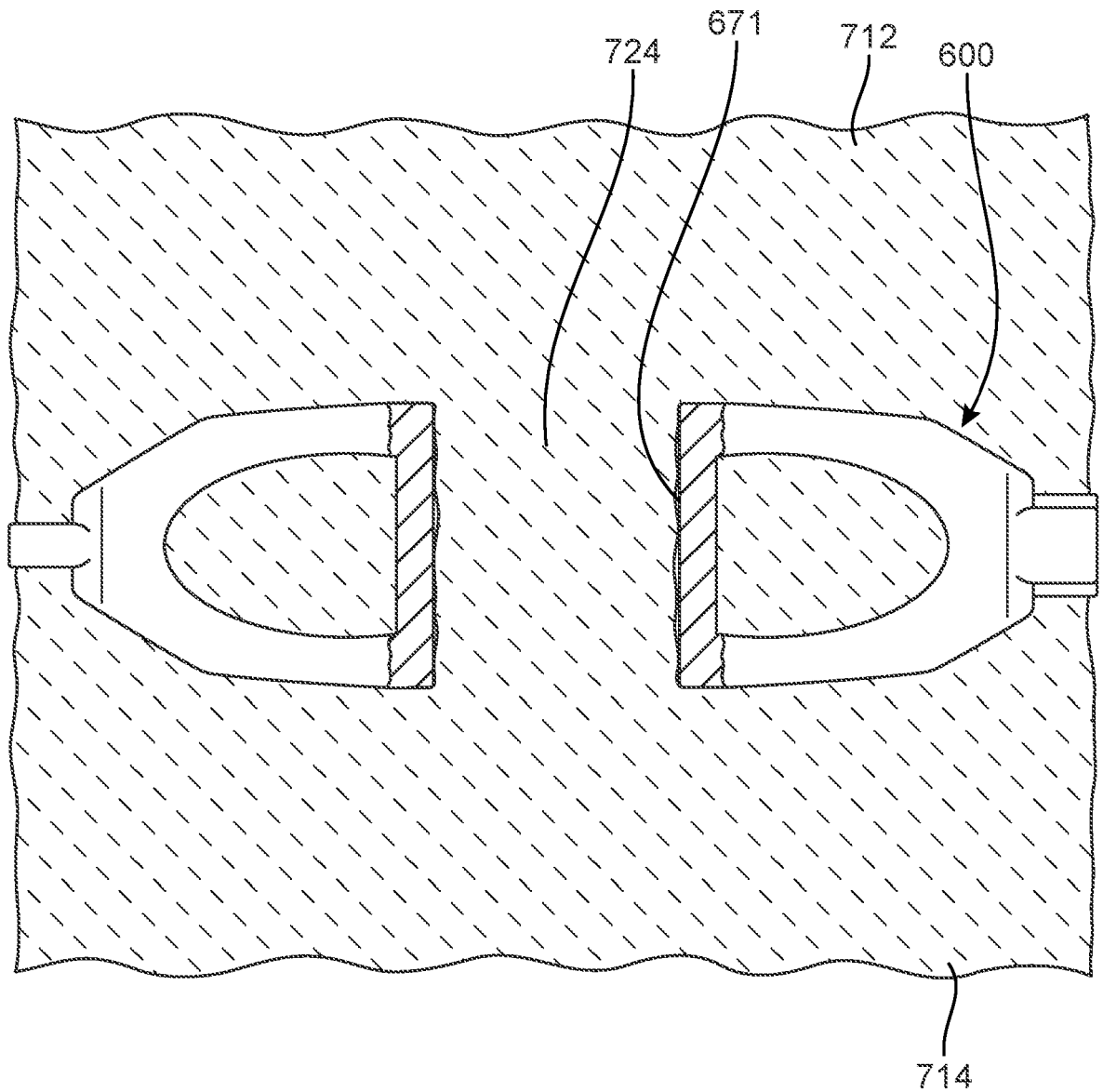
FIG. 16 is a schematic side view of the implant of FIG. 13 indicating areas of new bone growth.

FIGS. 14-16 depict a partial cross-sectional view of implant 600 just after implantation between vertebra 712 and vertebra 714. Here, BGPM 700 fills an interior of implant 600 and also coats the superior and inferior surfaces in contact with the vertebrae.

Initial bone fusion and growth may occur where the vertebrae are in contact with BGPM 700. With time, new bone growth begins to extend along the inferior and superior surfaces of implant 600 as well as into central cavity 671, as seen in FIG. 15. For example, in FIG. 15, new bone growth region 720 extends from vertebra 712 into central cavity 671 while new bone growth region 722 extends from vertebra 714 into central cavity 671. New bone growth regions 726 may also extend into the interior spaces of implant 600 that are adjacent to central cavity 671.

Eventually, as seen in FIG. 16, a solid column of new bone growth 724 may form throughout central cavity 671. This new bone growth in central cavity 671, along with new bone growth associated with other regions of the interior and exterior of implant 600, helps to fuse vertebra 712 and vertebra 714.

FIGS. 17-20 depict a schematic sequence of bone growth along a superior surface 675 of implant 600. This new bone growth may occur prior to, simultaneously with, or after bone has grown through the interior of implant 600 as described above. While only the superior side is shown in FIGS. 17-20, it may be appreciated that similar bone growth patterns may occur on the inferior side of the implant simultaneously.

Figure 17:
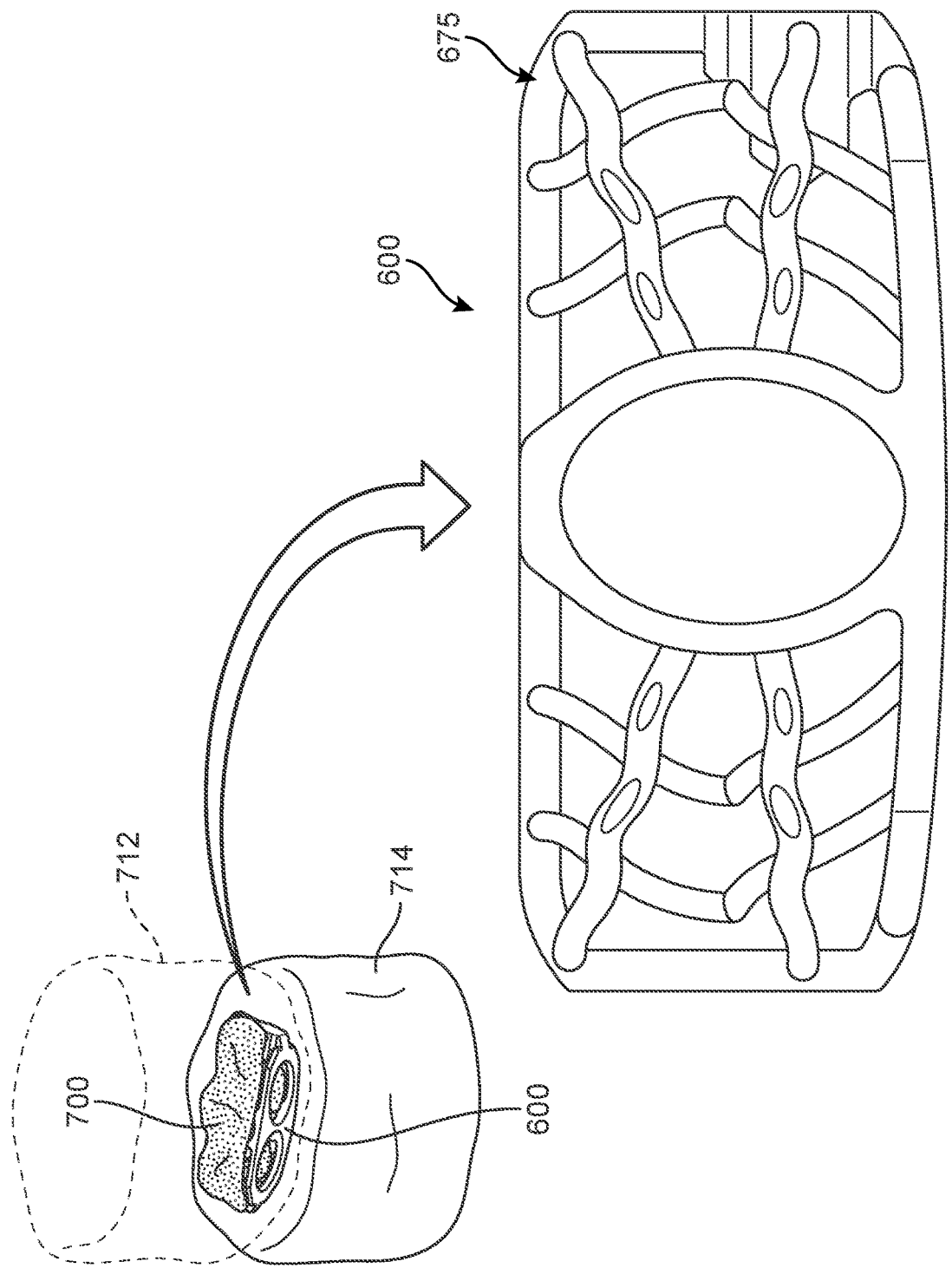
FIG. 17 is a schematic isometric view of the implant of FIG. 13 including an enlarged view of the superior side of the implant.

FIG. 17 depicts an isometric view of implant 600 inserted between vertebra 712 and vertebra 714 as well as an enlarged view of superior surface 675. It may be appreciated that, BGPM 700 is not visible in the enlarged view in FIG. 17. This is done for clarity so that new bone growth can be clearly seen as it forms along the surface of structural members of implant 600.

Figure 18:
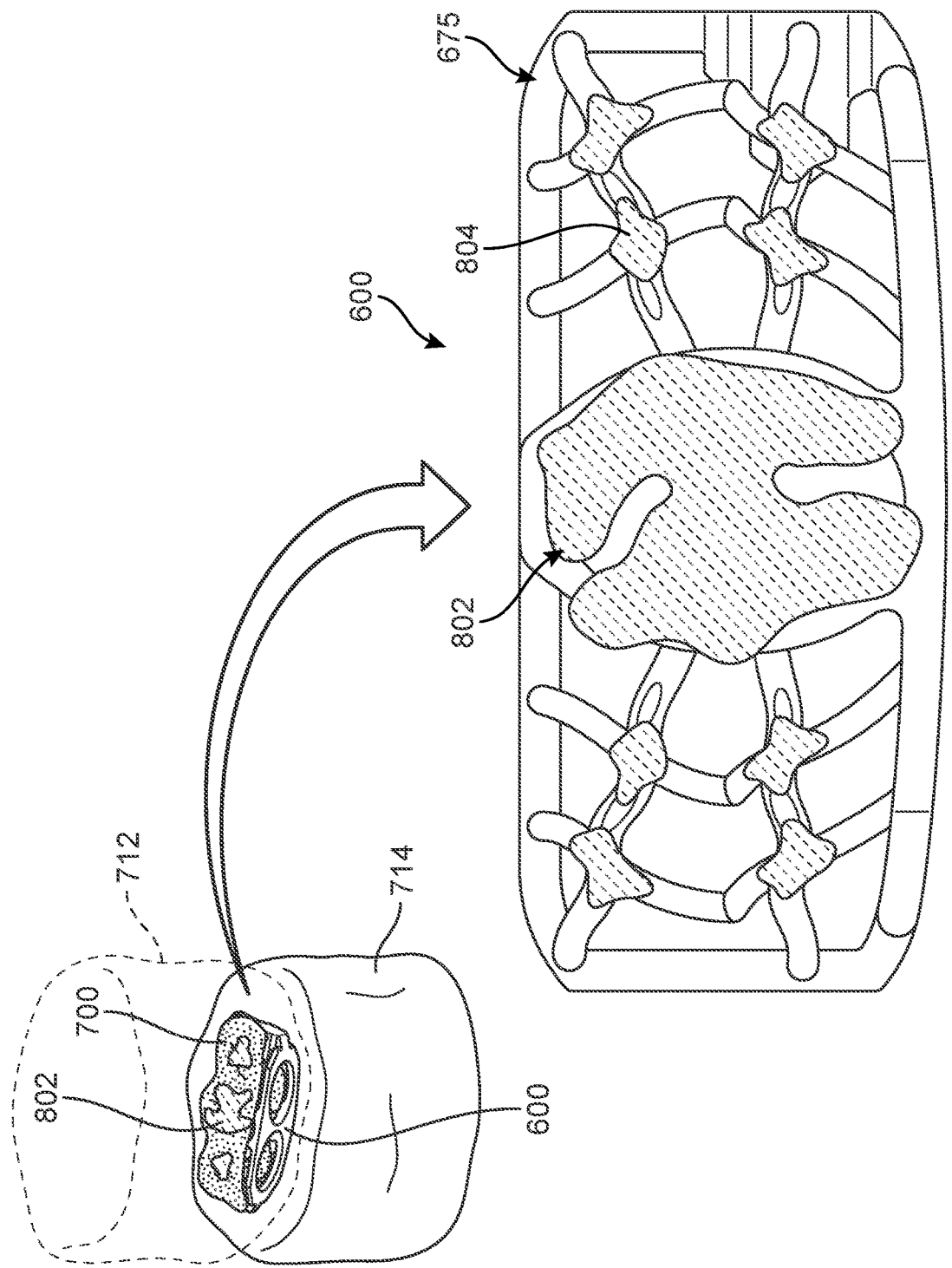
FIG. 18 is a schematic isometric view of the implant of FIG. 13 indicating areas of new bone growth on the superior side of the implant.

In FIG. 18, new bone growth occurs in multiple locations on superior surface 675. Specifically, new bone growth region 802 occurs within central cavity 671, as described above and depicted in FIGS. 14-16. In addition, new bone growth regions 804 may first form at the protected fusion zones discussed earlier. As disclosed in The Protected Fusion Zone Application, new bone growth regions 804 occurring in protected fusion zones may be protected from local forces between bone contacting members and the vertebrae. This helps minimize the disturbance to new bone growth regions 804 in the protected fusion zones.

Figure 19:
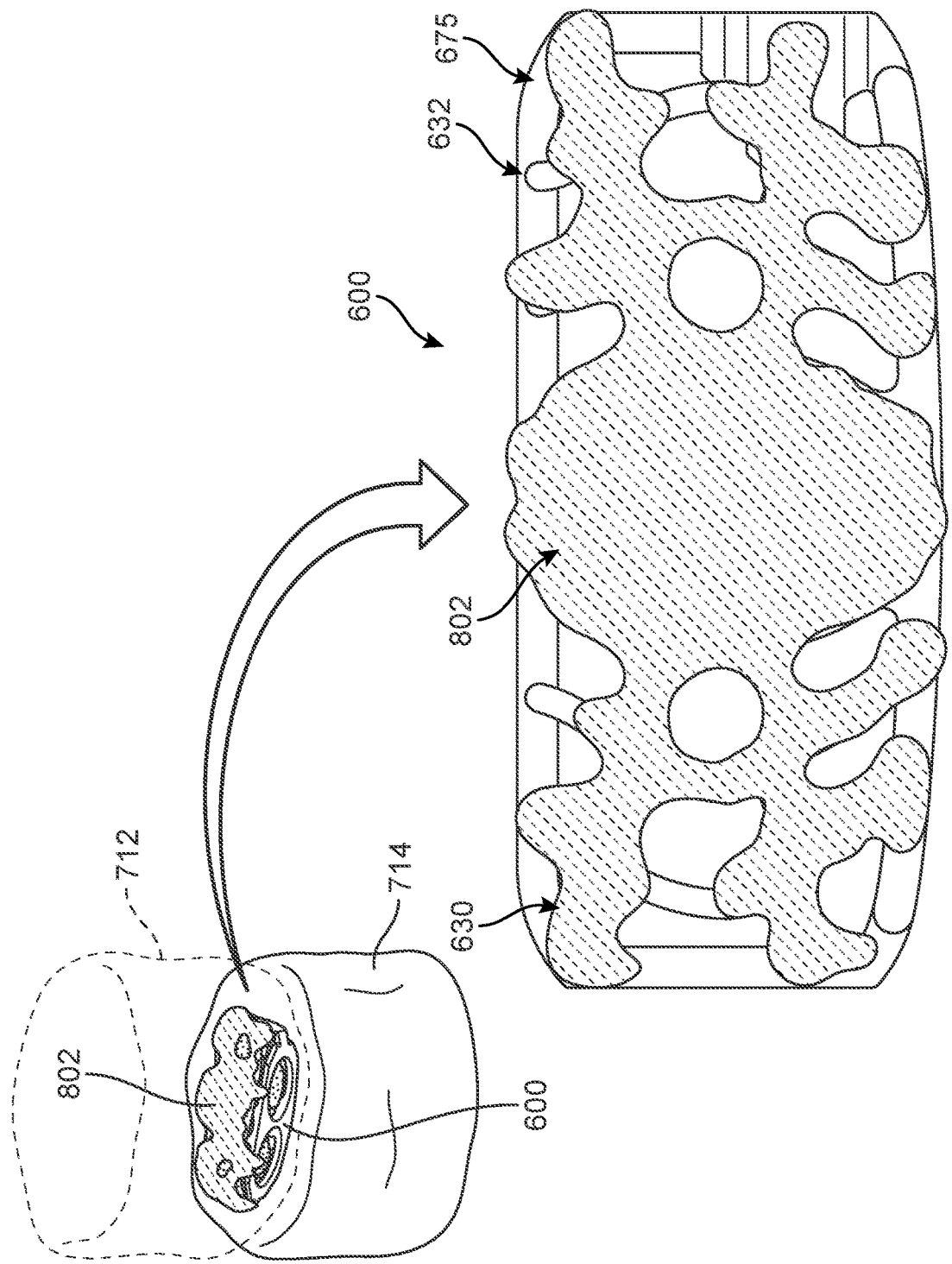
FIG. 19 is a schematic isometric view of the implant of FIG. 13 indicating areas of new bone growth on the superior side of the implant.

As shown in FIG. 19, eventually, new bone growth may extend from the protective fusion zones to the entire length of plurality of bone contacting members 630. In some embodiments, new bone growth may continue to grow along the surfaces of plurality of support members 632 as well.

It may be appreciated that new bone growth similarly occurs on the inferior surface of implant 600, as well as extending around the lateral, posterior and anterior sides.

Figure 20:
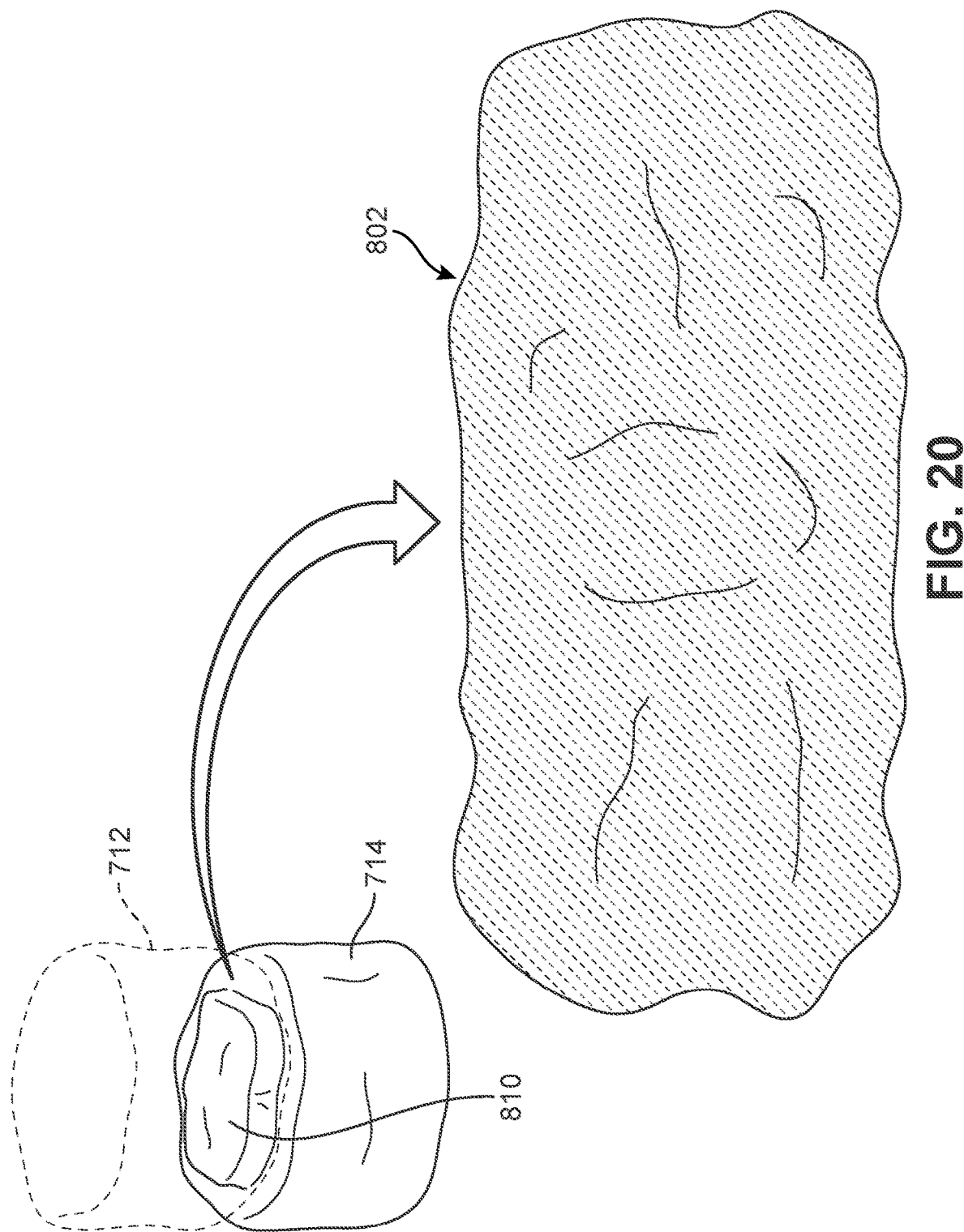
FIG. 20 is a schematic isometric view of new bone growth covering the implant of FIG. 13.

Finally, as seen in FIG. 20, new bone growth region 802 may cover the exterior, and fill the interior, of an implant. At this point, there may be a new bone fusion portion 810 that extends between vertebra 712 and vertebra 714 that fuses the vertebrae together.

In some other embodiments, increased volume for bone graft material and eventually new bone growth may be created by removing one or more structures that are disposed within an internal region of an implant. For example, in another embodiment, the structures connecting superior and inferior rings (e.g., first support 226 and second support 228 shown in FIG. 3) could be removed. Still other modifications could be made to incorporate any of the structures and/or arrangements as disclosed in U.S. Pat. No. 10,213,317, issued on Feb. 26, 2019, and titled "Implant with Supported Helical Members," which is hereby incorporated by reference in its entirety.

Embodiments can include provisions for texturing one or more surfaces of an implant. Such texturing can increase or otherwise promote bone growth and/or fusion to surfaces of the implant. In some embodiments, bone contacting members may be textured while support members may not be textured. This helps initial bone growth to be directed along the bone contacting members and especially into the protected fusion zones, rather than growing initially across support members. In other embodiments, however, support members could include surface texturing. In still further embodiments, one or more surfaces of a body could include surface texturing.

In some embodiments, the surface structure of one or more regions of an implant may be roughened or provided with irregularities. Generally, this roughened structure may be accomplished through the use of acid etching, bead or grit blasting, sputter coating with titanium, sintering beads of titanium or cobalt chrome onto the implant surface, as well as other methods. In some embodiments, the roughness can be created by 3D printing a raised pattern on the surface of one or more regions of an implant. In some embodiments, the resulting roughened surface may have pores of varying sizes. In some embodiments, pore sizes could range between approximately 0.2 mm and 0.8 mm. In one embodiment, pore sizes could be approximately 0.5 mm. In other embodiments, surface roughness comprising pore sizes less than 0.2 mm and/or greater than 0.8 mm are possible.

The embodiments can make use of the surface texturing parts, features, processes or methods as disclosed in The Protected Fusion Zone Application.

The implants for use in the spine have overall dimensions suitable for insertion in the spine, typically between two vertebral bodies. The shape of the implant and dimensions depends on the site into which it is inserted. Exemplary heights for implants such as implant 100 and implant 600 include, but are not limited to, 5 mm to 30 mm. Other embodiments could have incremental heights of any value in the range between the aforementioned range, most often between 8 mm and 16 mm. Still other embodiments could have a height greater than 16 mm. Still other embodiments could have a height less than 8 mm. Additionally, the horizontal footprint of the implant could vary. Exemplary footprint sizes for any embodiments of the implant include, but are not limited to, 15-20 mm in the anterior-posterior direction and 40-60 mm in the lateral-lateral direction. Still other embodiments could be configured with any other footprint sizes.

The dimensions of one or more structural members could vary. In some embodiments, a structural member could have a cross-sectional diameter in a range between 0.2 and 3 mm. For structural members with polygonal cross sections, the dimensions characterizing the polygon (e.g., first and second diameters for an ellipse) could vary. As an example, a structural member with an elliptic cross section could have a cross section with a first diameter in a range between 0.2 mm and 3 mm and a second diameter in range between 0.2 mm and 3 mm. In other embodiments, a structural member could have any other cross-sectional diameter. Moreover, in some cases a bone contacting member and a support member could have similar cross-sectional diameters while in other cases a bone contacting member and a support member could have different cross-sectional diameters.

Embodiments can also be provided with various flat/parallel (0-degree), lordotic, and hyper-lordotic angles. In some embodiments, the implant can be configured with an approximately 8-degree angle between the superior and inferior surfaces. In other embodiments, the implant can be configured with an approximately 15-degree angle between the superior and inferior surfaces. In still other embodiments, the implant can be configured with an approximately 20-degree angle between the superior and inferior surfaces. Still other angles are possibly including any angles in the range between 0 and 30 degrees. Still other embodiments can provide a lordotic angle of less than 8 degrees. Still other embodiments can provide a hyper-lordotic angle of more than 20 degrees. In at least some embodiments, the lordotic angle of the implant is accomplished via the geometry of the central keel portion and the side frame portion (posterior or anterior).

The various components of an implant may be fabricated from biocompatible materials suitable for implantation in a human body, including but not limited to, metals (e.g. titanium or other metals), synthetic polymers, ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g. γTitanium Aluminides, $Ti_6$-$Al_4$-V ELI (ASTM F 136 and F 3001), or $Ti_6$-$Al_4$-V (ASTM F 2989, F 1108 and ASTM F 1472)) and inert, biocompatible polymers, such as polyether ether ketone (PEEK) (e.g. PEEK-OPTIMA®, Invibio Inc and Zeniva Solvay Inc.). Optionally, the implant contains a radiopaque marker to facilitate visualization during imaging.

In different embodiments, processes for making an implant can vary. In some embodiments, the entire implant may be manufactured and assembled via readditional/CNC machining, injection-molding, casting, insert-molding, co-extrusion, pultrusion, transfer molding, overmolding, compression molding, 3-Dimensional (3-D) printing (including Direct Metal Laser Sintering and Electron Beam Melting), dip-coating, spray-coating, powder-coating, porous-coating, milling from a solid stock material and their combinations. Moreover, the embodiments can make use of any of the features, parts, assemblies, processes and/or methods disclosed in the "The Coiled Implant Application".

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. An implant, comprising:
   a body including a ring, the ring further defining an opening;
   the body defining a transverse plane dividing the implant into a superior half and an inferior half;
   the ring defining a radial direction and a circumferential direction;
   a first outer member attached to the ring, wherein the first outer member extends radially from the ring;
   wherein the first outer member defines one or more arches; and
   wherein the ring further defines a central channel extending through the implant.

2. The implant according to claim 1, wherein the central channel extends from a superior side to an inferior side of the implant.

3. The implant according to claim 1, wherein the one or more arches of the first outer member extend in a superior direction.

4. The implant according to claim 1, wherein the body includes a peripheral frame portion that defines an outer periphery of the implant; and wherein the first outer member extends from the ring to the peripheral frame portion.

5. The implant according to claim 1, wherein the first outer member has a generally helical geometry defining a plurality of arches.

6. The implant according to claim 5, wherein the implant further includes a second outer member, a third outer member, and a fourth outer member.

7. The implant according to claim 6, wherein the first outer member and the second outer member extend from a first side of the ring to a first end of the implant, and wherein the third outer member and the fourth outer member extend from a second side of the ring to a second end of the implant.

8. The implant according to claim 7, wherein the implant further includes a plurality of supports, wherein each of the plurality of supports are attached to at least one outer member, and wherein each of the plurality of supports extend in the circumferential direction.

9. The implant according to claim 8, wherein the first outer member, the second outer member, the third outer member, the fourth outer member and the plurality of supports are arranged in a web-like pattern.

10. The implant according to claim 9, wherein the web-like pattern is disposed in the superior half of the implant, and wherein the implant has another web-like pattern formed of outer members and supports disposed in the inferior half of the implant.

11. The implant according to claim 1, further including a support attached to the first outer member at an attachment region, wherein the support extends in the circumferential direction.

12. The implant according to claim 11, wherein, at the attachment region, the support is disposed closer to the transverse plane than the first outer member is to the transverse plane.

13. An implant, comprising:
a body;
the body defining a transverse plane dividing the implant into a superior half and an inferior half;
a first outer member attached to the body and disposed within the superior half of the implant;
a first support attached to the first outer member, the first support being disposed within the superior half of the implant;
a second outer member attached to the body and disposed within the inferior half of the implant;
a second support attached to the second outer member, the second support being disposed within the inferior half of the implant;
wherein an end of the first support is attached to an end of the second support; and
wherein the first outer member and the second outer member each form one or more arches;
wherein the implant includes a first ring disposed in the superior half, wherein the first outer member is attached to the first ring;
the implant includes a second ring disposed in the inferior half, wherein the second outer member is attached to the second ring;
wherein the first ring and the second ring define a central channel extending through the implant.

14. The implant according to claim 13, wherein the first ring is joined to the second ring by additional supports extending through the transverse plane, such that the first ring and the second ring define openings for the central channel extending through the implant.

15. The implant according to claim 13, wherein the central channel extends from a superior side to an inferior side of the implant.

16. The implant according to claim 13, wherein the one or more arches of the first outer member extend in a superior direction.

17. An implant, comprising:
a body;
the body defining a transverse plane dividing the implant into a superior half and an inferior half;
a plurality of outer members disposed within the superior half of the implant and extending from a central region of the body to a periphery of the body; and
wherein each of the outer members in the plurality of outer members extend radially away from the central region of the body;
wherein each of the plurality of outer members form one or more arches; and
wherein the implant includes at least one ring disposed in the central region of the body and defining a central channel extending through the implant from a superior side to an inferior side of the body.

18. The implant according to claim 17, wherein the implant includes three or more outer members.

19. The implant according to claim 17, wherein the body includes a peripheral frame portion that defines an outer periphery of the implant; and
wherein the outer members extend from the at least one ring to the peripheral frame portion.

20. The implant according to claim 17, wherein the implant further includes a plurality of supports, wherein each of the plurality of supports are attached to at least one outer member, and wherein each of the plurality of supports extend in a circumferential direction defined by the at least one ring.

* * * * *